United States Patent [19]

Takematsu et al.

[11] Patent Number: 4,554,012
[45] Date of Patent: Nov. 19, 1985

[54] ARYL N-ALKYL-N-(PYRIDYL OR PYRIMIDYL) CARBAMATE

[75] Inventors: Tetsuo Takematsu; Konnai, Makoto; Hideo Morinaka, all of Utsunomiya; Yuji Nonaka, Shinnanyo; Akira Nakanishi, Shinnanyo; Kenji Tsuzuki, Shinnanyo; Mitsuyuki Hashihama, Shinnanyo; Takeshi Uwotani, Shinnanyo, all of Japan

[73] Assignee: Toyo Soda Manufacturing Co., Ltd., Shinnanyo, Japan

[21] Appl. No.: 502,170

[22] Filed: Jun. 8, 1983

[30] Foreign Application Priority Data

Jun. 10, 1982 [JP] Japan ................ 57-98485
Jul. 27, 1982 [JP] Japan ................ 57-129651
Sep. 10, 1982 [JP] Japan ................ 57-156710
Mar. 4, 1983 [JP] Japan ................ 58-34651

[51] Int. Cl.$^4$ .................. A01N 43/48; C07D 239/72
[52] U.S. Cl. ........................ 71/92; 544/283; 544/331; 544/332; 546/157; 546/256; 71/94
[58] Field of Search ............. 546/157, 256; 544/283, 544/331, 332; 71/92, 94

[56] References Cited

U.S. PATENT DOCUMENTS

| 3,334,126 | 8/1967 | Miyazaki et al. | 424/300 |
| 3,509,200 | 4/1970 | Elpern et al. | 424/278 |
| 3,538,099 | 11/1970 | Rohr | 424/258 |
| 3,855,263 | 12/1974 | Melloni et al. | 424/300 |
| 3,938,986 | 2/1976 | Pray | 71/94 |
| 4,168,311 | 9/1979 | Studeneer et al. | 424/258 |

FOREIGN PATENT DOCUMENTS

| 3018670 | 11/1981 | Fed. Rep. of Germany . |
| 3318560 | 12/1983 | Fed. Rep. of Germany . |
| 4849925 | 7/1973 | Japan . |
| 108851 | 8/1980 | Japan . |

OTHER PUBLICATIONS

Chem. Abst. vol. 94 (1981), p. 644, 156757d, Eqiv. to Japan 80108851.
Chem. Abst. vol. 100 (1984), 103184a, Equiv. to DE 3318560 (German).
Hodogaya Chemical Co., Ltd., "Short Review of Herbicides", (1982) pp. 3-5.
Yakugaku Zasshi 88 335 (1968), "Studies on the Selective Toxicity II . . . ", Noguchi et al, pp. 335-343.
Takugaku Zasshi 88 344 (1968), "Studies on the Selective Toxicity III . . . ", Noguchi et al, pp. 344-352.
Yakugaku Zasshi 88 465 (1968), "Studies on the Selective Toxicity V . . . ", Noguchi et al, pp. 465-472.

Primary Examiner—Donald G. Daus
Assistant Examiner—Cecilia Shen
Attorney, Agent, or Firm—Oblon, Fisher, Spivak, McClelland & Maier

[57] ABSTRACT

Carbamate derivatives represented by the general formula (I);

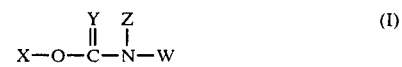

wherein
X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or substituted phenyl,
Y is an oxygen atom or a sulfur atom,
Z is lower alkyl,
W is pyridyl or pyrimidyl which is unsubstituted or substituted; process for the preparation of such compounds;

and herbicides containing the same as an active ingredient.

9 Claims, No Drawings

ARYL N-ALKYL-N-(PYRIDYL OR PYRIMIDYL) CARBAMATE

DETAILED EXPLANATION OF THE INVENTION

The present invention concerns carbamate derivatives, process for the preparation of such compounds, and herbicides comprising the same as an active ingredient.

Hitherto, it has been well-known that arylthiocarbamate derivatives have antifungal activity as drugs and also that aryl N-arylcarbamate derivatives can be used as herbicides.

The present inventors found and reported earlier that some N-pyridylcarbamate derivatives have herbicidal activity. Furthermore, the present invention was completed by earnestly conducted investigation to develop N-pyridylcarbamate and N-pyrimidylcarbamate derivatives which exhibited sufficient herbicidal activity and high selectivity.

More especially, the present invention provides carbamate derivatives represented by the general formula (I) (hereinafter referred to as the compounds of the present invention):

wherein
X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or substituted phenyl having one or more than one of the same or different substituents selected from the group of halogeno, lower alkyl, lower alkenyl, lower alkoxy, lower alkenyloxy, lower alkynyloxy, lower alkylthio, lower alkylamino, (hydroxy-lower alkyl, (lower alkoxy-lower alkyl, acyl, nitro, cyano, methylenedioxy, and halogenated lower alkyl,
Y is an oxygen atom or a sulfur atom,
Z is lower alkyl,
W is pyridyl substituted by one or two of the same substituents selected from the group of halogeno, lower alkyl, and lower alkylamino when X is 2-naphthyl but W is pyridyl or pyrimidyl which is unsubstituted or substituted by one or two of the same or different substituents selected from the group of halogeno, nitro, lower alkyl, lower alkoxy, lower alkylthio, and lower alkylamino when X is other than 2-naphthyl,
process for the preparation of such compounds, and herbicides containing the same as an active ingredient.

The herbicides containing the compounds of the present invention show extremely excellent herbicidal activity against barnyard grass as well as many general weeds in the flooded paddy field, and they are substantially harmless against transplanted rice plants. Therefore, these herbicides are suitable for use in the paddy field. In addition, the herbicides containing the compounds of the present invention were recognized to have an applicability to be used in the farmland from the observation that they showed excellent herbicidal selectivity between gramineous weeds and broadleaved crops in the soil treatment of the farmland.

The carbamate derivatives of the present invention represented by the general formula (I) can be prepared according to the following reaction equations (1) and (2):

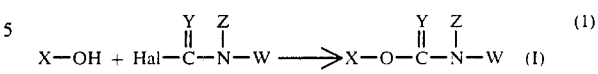

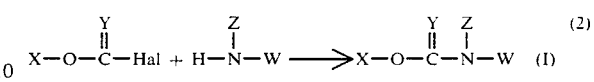

wherein
X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, 2-quinolyl, or substituted phenyl having one or more than one of the same or different substituents selected from the group of halogeno, lower alkyl, lower alkenyl, lower alkoxy, lower alkenyloxy, lower alkynyloxy, lower alkylthio, lower alkylamino, hydroxy, -lower alkyl, lower alkoxy, -lower alkyl, acyl, nitro, cyano, methylenedioxy, and halogenated lower alkyl,
Y is an oxygen atom or a sulfur atom,
Z is lower alkyl,
W is pyridyl substituted by one or two of the same substituents selected from the group of halogeno, lower alkyl, and lower alkylamino when X is 2-naphthyl but W is pyridyl or pyrimidyl which is unsubstituted or substituted by one or two of the same or different substituents selected from the group of halogeno, nitro, lower alkyl, lower alkoxy, lower alkylthio, and lower alkylamino when X is other than 2-naphthyl,
Hal is a halogen atom.

The above-stated reactions proceed in the presence of dehydrohalogenation agents and further in the presence or absence of reaction solvents usually at the reaction temperature ranging from 0° to 150° C. during the reaction time ranging from about few minutes to 48 hours.

As the dehydrohalogenation agents, alkali hydroxides such as sodium hydroxide, potassium hydroxide and the like; alkali earth hydroxides such as calcium hydroxide and the like; alkali carbonates such as sodium carbonate, potassium carbonate, sodium bicarbonate, potassium bicarbonate and the like; metal hydrides such as sodium hydride and the like; and tertiary amines such as triethylamine, N,N-dimethylaniline, pyridine and the like can be exemplified. The starting amine derivatives can be used as the dehydrohalogenation agents in the reaction shown by the equation (2).

As the reaction solvents, water; alcohols such as methanol, ethanol, isopropanol and the like; ketones such as acetone, methyl ethyl ketone and the like; aromatic hydrocarbons such as benzene, toluene, xylene, and the like; ethers such as ethyl ether, tetrahydrofuran, dioxane and the like; halogenated hydrocarbons such as chlorobenzene; chloroform, carbon tetrachloride, dichloroethane and the like; and polar solvents such as dimethylformamide, dimethylsulfoxide and the like can be used.

Typical procedures for the preparation of the compounds of the present invention are explained in detail herein-below.

EXAMPLES

EXAMPLE 1

Preparation of 4-isopropylphenyl N-(6-methoxy-2-pyridyl)-N-methylcarbamate (Compound No. 59)

A mixture of 2.01 g of N-(6-methoxy-2-pyridyl)-N-methylcarbamoylchloride, 1.36 g of 4-isopropylphenol, and 1.38 g of anhydrous potassium carbonate in 50 ml of methyl ethyl ketone was refluxed for 5 hours. After the reaction mixture was cooled to room temperature, it was poured into cold water and the product was extracted with benzene. The benzene solution, successively washed with water and brine, was dried over anhydrous magnesium sulfate. The residue obtained by the removal of benzene under reduced pressure was chromatographed through silica gel column using benzene as an eluent to give 2.56 g of pure 4-isopropylphenyl N-(6-methoxy-2-pyridyl)-N-methylcarbamate as solid in the yield of 85%. A part of the solid was recrystallized from hexane and crystals having melting point of 64° to 65° C. were obtained.

EXAMPLE 2

Preparation of O-4-chloro-3-methylphenyl N-methyl-N-(6-methyl-2-pyridyl)thiocarbamate (Compound No. 114)

A mixture of 2.01 g of N-methyl-N-(6-methyl-2-pyridyl)thiocarbamoylchloride, 1.43 g of 4-chloro-3-methylphenol, and 1.38 g of potassium carbonate in 50 ml of methyl ethyl ketone was refluxed for 48 hours. After the reaction mixture was cooled to room temperature, it was poured into cold water and the product was extracted with benzene. The benzene solution, successively washed with water and brine, was dried over anhydrous magnesium sulfate. The residue obtained by the removal of benzene under reduced pressure was chromatographed through silica gel column using hexane-ethyl acetate (3/1, V/V) as an eluent to give 1.07 g of pure O-4-chloro-3-methylphenyl N-methyl-N-(6-methyl-2-pyridyl)thiocarbamate as solid in the yield of 35%. A part of the solid was recrystallized from benzene-hexane and crystals having melting point of 134° to 136° C. were obtained.

EXAMPLE 3

Preparation of 4-trifluoromethylphenyl N-(6-methoxy-2-pyridyl)-N-methylcarbamate (Compound No. 97)

To the mixture of 1.38 g of 2-methoxy-6-methylaminopyridine and 1.38 g of anhydrous potassium carbonate in 20 ml of acetone was added dropwise the solution of 2.25 g of 4-trifluoromethylphenyl chloroformate in 20 ml of acetone under stirring at room temperature. The mixture was stirred for 30 minutes and then was refluxed for 2 hours. After the reaction mixture was cooled to room temperature, it was poured into water and the product was extracted with benzene. The benzene solution, successively washed with water and brine, was dried over anhydrous magnesium sulfate. The residue obtained by the removal of benzene under reduced pressure was chromatographed through silica gel column using benzene as an eluent to give 2.02 g of pure 4-trifluoromethylphenyl N-(6-methoxy-2-pyridyl)-N-methylcarbamate as solid in the yield of 62%. A part of the solid was recrystallized from hexane and crystals having melting point of 85° to 86° C. were obtained.

EXAMPLE 4

Preparation of O-3,4-dimethylphenyl N-methyl-N-(4-methyl-2-pyridyl)thiocarbamate (Compound No. 115)

To the mixture of 1.22 g of 4-methyl-2-methylaminopyridine and 1.38 g of anhydrous potassium carbonate in 20 ml of acetone was added dropwise the solution of 2.01 g of O-3,4-dimethylphenyl chlorothioformate in 20 ml of acetone under stirring at room temperature. The mixture was stirred for 30 minutes and then was refluxed for 2 hours. After the reaction mixture was cooled to room temperature, it was poured into cold water and the product was extracted with benzene. The benzene solution, successively washed with water and brine, was dried over anhydrous magnesium sulfate. The residue obtained by the removal of benzene under reduced pressure was chromatographed through silica gel column using hexane-ethyl acetate (3/1, V/V) as an eluent to give 2.24 g of pure O-3,4-dimethylphenyl-methyl-N-(4-methyl-2-pyridyl)thiocarbamate as solid in the yield of 78%. A part of the solid was recrystallized from benzene-hexane and crystals having melting point of 113° to 114° C. were obtained.

Typical examples of the compounds of the present invention having numbers of an identification are listed herein-below and those physical properties together with elemental analysis are shown in Table 1.

| NO. | THE COMPOUNDS OF THE PRESENT INVENTION |
|---|---|
| 1. | 2-Naphthyl N—methyl-N—(6-methyl-2-pyridyl)carbamate |
| 2. | 2-Naphthyl N—methyl-N—(3-methyl-2-pyridyl)carbamate |
| 3. | O-2-Naphthyl N—methyl-N—(6-methyl-2-pyridyl)thiocarbamate |
| 4. | O-2-Naphthyl N—methyl-N—(4-methyl-2-pyridyl)thiocarbamate |
| 5. | O-5-Indanyl N—methyl-N—(6-methyl-2-pyridyl)thiocarbamate |
| 6. | O-5,6,7,8-Tetrahydro-2-naphthyl N—methyl-N—(6-methyl-2-pyridyl)thiocarbamate |
| 7. | O-5-Indanyl N—methyl-N—(5-methyl-2-pyridyl)thiocarbamate |
| 8. | O-5,6,7,8-Tetrahydro-2-naphthyl N—methyl-N—(5-methyl-2-pyridyl)thiocarbamate |
| 9. | O-5-Indanyl N—methyl-N—(4-methyl-2-pyridyl)thiocarbamate |
| 10. | O-5,6,7,8-Tetrahydro-2-naphthyl N—methyl-N—(4-methyl-2-pyridyl)thiocarbamate |
| 11. | O-5-Indanyl N—methyl-N—(3-methyl-2-pyridyl)thiocarbamate |
| 12. | O-5,6,7,8-Tetrahydro-2-naphthyl N—methyl-N—(3-methyl-2-pyridyl)thiocarbamate |
| 13. | O-5-Indanyl N—(6-methoxy-2-pyridyl)-N—methylthiocarbamate |
| 14. | O-5,6,7,8-Tetrahydro-2-naphthyl N—(6-methoxy-2-pyridyl)-N—methylthiocarbamate |
| 15. | O-1,4-Methano-1,2,3,4-tetrahydro-6-naphthyl N—(6-methoxy-2-pyridyl)-N—methylthiocarbamate |
| 16. | 5-Indanyl N—(6-methoxy-2-pyridyl)-N—methylcarbamate |

-continued

| NO. | THE COMPOUNDS OF THE PRESENT INVENTION |
|---|---|
| 17. | 5,6,7,8-Tetrahydro-2-naphthyl N—(6-methoxy-2-pyridyl)-N—methylcarbamate |
| 18. | 1,4-Methano-1,2,3,4-tetrahydro-6-naphthyl N—(6-methoxy-2-pyridyl)-N—methylcarbamate |
| 19. | O-2-Naphthyl-N—methyl-N—(4,6-dimethyl-2-pyridyl)thiocarbamate |
| 20. | O-5,6,7,8-Tetrahydro-2-naphthyl N—methyl-N—(4,6-dimethyl-2-pyridyl)thiocarbamate |
| 21. | O-5-Indanyl N—methyl-N—(4,6-dimethyl-2-pyridyl)thiocarbamate |
| 22. | O-2-Naphthyl N—(6-chloro-2-pyridyl)-N—methylthiocarbamate |
| 23. | O-5,6,7,8-Tetrahydro-2-naphthyl N—(6-chloro-2-pyridyl)-N—methylthiocarbamate |
| 24. | 5,6,7,8-Tetrahydro-2-naphthyl N—(6-chloro-2-pyridyl)-N—methylcarbamate |
| 25. | O-5-Indanyl N—(6-chloro-2-pyridyl)-N—methylthiocarbamate |
| 26. | O-5-Indanyl N—methyl-N—(2-pyridyl)thiocarbamate |
| 27. | O-5,6,7,8-Tetrahydro-2-naphthyl N—methyl-N—(2-pyridyl)thiocarbamate |
| 28. | O-4-tert-Butylphenyl N—(6-methoxy-2-pyridyl)-N—methylthiocarbamate |
| 29. | O-4-tert-Butylphenyl N—methyl-N—(2-pyridyl)thiocarbamate |
| 30. | O-4-tert-Butylphenyl N—methyl-N—(6-methyl-2-pyridyl)thiocarbamate |
| 31. | O-4-tert-Butylphenyl N—methyl-N—(5-methyl-2-pyridyl)thiocarbamate |
| 32. | O-4-tert-Butylphenyl N—methyl-N—(4-methyl-2-pyridyl)thiocarbamate |
| 33. | O-4-tert-Butylphenyl N—methyl-N—(3-methyl-2-pyridyl)thiocarbamate |
| 34. | O-4-tert-Butylphenyl N—methyl-N—(4,6-dimethyl-2-pyridyl)thiocarbamate |
| 35. | 4-tert-Butylphenyl N—(6-methoxy-2-pyridyl)-N—methylcarbamate |
| 36. | O-4-tert-Pentylphenyl N—(6-methoxy-2-pyridyl)-N—methylthiocarbamate |
| 37. | O-5,6,7,8-Tetrahydro-2-naphthyl N—(6-bromo-2-pyridyl)-N—methylthiocarbamate |
| 38. | O-1,4-Ethano-1,2,3,4-tetrahydro-6-naphthyl N—(6-methoxy-2-pyridyl)-N—methylthiocarbamate |
| 39. | O-3,4-Dimethylphenyl N—(6-methoxy-2-pyridyl)-N—methylthiocarbamate |
| 40. | 3,4-Dimethylphenyl N—(6-methoxy-2-pyridyl)-N—methylcarbamate |
| 41. | O-5-Indanyl N—(4-ethyl-2-pyridyl)-N—methylthiocarbamate |
| 42. | O-5,6,7,8-Tetrahydro-2-naphthyl N—(4-ethyl-2-pyridyl)-N—methylthiocarbamate |
| 43. | O-2-Naphthyl N—(6-ethyl-2-pyridyl)-N—methylthiocarbamate |
| 44. | O-5-Indanyl N—(6-ethyl-2-pyridyl)-N—methylthiocarbamate |
| 45. | O-5,6,7,8-Tetrahydro-2-naphthyl N—(6-ethyl-2-pyridyl)-N—methylthiocarbamate |
| 46. | O-4-tert-Butylphenyl N—(6-ethyl-2-pyridyl)-N—methylthiocarbamate |
| 47. | O-2-Naphthyl N—methyl-N—(5,6-dimethyl-2-pyridyl)thiocarbamate |
| 48. | O-5-Indanyl Naphthyl-N—(5,6-dimethyl-2-pyridyl)thiocarbamate |
| 49. | O-5,6,7,8-Tetrahydro-2-naphthyl N—methyl-N—(5,6-dimethyl-2-pyridyl)thiocarbamate |
| 50. | O-4-tert-Butylphenyl N—methyl-N—(5,6-dimethyl-2-pyridyl)thiocarbamate |
| 51. | O-3-tert-Butylphenyl N—(6-methoxy-2-pyridyl)-N—methylthiocarbamate |
| 52. | 3-tert-Butylphenyl N—(6-methoxy-2-pyridyl)-N—methylcarbamate |
| 53. | O-4-tert-Butylphenyl N—(6-bromo-2-pyridyl)-N—methylthiocarbamate |
| 54. | O-4-tert-Butylphenyl N—(6-chloro-2-pyridyl)-N—methylthiocarbamate |
| 55. | 4-tert-Pentylphenyl N—(6-methoxy-2-pyridyl)-N—methylcarbamate |
| 56. | O-4-sec-Butylphenyl N—(6-methoxy-2-pyridyl)-N—methylthiocarbamate |
| 57. | 4-sec-Butylphenyl N—(6-methoxy-2-pyridyl)-N—methylcarbamate |
| 58. | O-4-Isopropylphenyl N—(6-methoxy-2-pyridyl)-N—methylthiocarbamate |
| 59. | 4-Isopropylphenyl N—(6-methoxy-2-pyridyl)-N—methylcarbamate |
| 60. | 1,4-Ethano-1,2,3,4-tetrahydro-6-naphthyl N—(6-methoxy-2-pyridyl)-N—methylcarbamate |
| 61. | O-3-Methylphenyl N—(6-methoxy-2-pyridyl)-N—methylthiocarbamate |
| 62. | O-3-Ethylphenyl N—(6-methoxy-2-pyridyl)-N—methylthiocarbamate |
| 63. | O-4-Ethylphenyl N—(6-methoxy-2-pyridyl)-N—methylthiocarbamate |
| 64. | O-4-Bromophenyl N—(6-methoxy-2-pyridyl)-N—methylthiocarbamate |
| 65. | 4-Bromophenyl N—(6-methoxy-2-pyridyl)-N—methylcarbamate |
| 66. | O-4-Bromo-3,5-dimethylphenyl N—(6-methoxy-2-pyridyl)-N—methylthiocarbamate |
| 67. | O-4-Chloro-3,5-dimethylphenyl N—(6-methoxy-2-pyridyl)-N—methylthiocarbamate |
| 68. | 1,4-Methano-1,2,3,4-tetrahydro-6-naphthyl N—(6-bromo-2-pyridyl)-N—methylcarbamate |
| 69. | O-2-Naphthyl N—methyl-N—(6-dimethylamino-2-pyridyl)thiocarbamate |
| 70. | O-5,6,7,8-Tetrahydro-2-naphthyl N—methyl-N—(6-dimethylamino-2-pyridyl)thiocarbamate |
| 71. | O-5-Indanyl N—methyl-N—(6-dimethylamino-2-pyridyl)thiocarbamate |
| 72. | O-4-tert-Butylphenyl N—methyl-N—(6-dimethylamino-2-pyridyl)thiocarbamate |
| 73. | O-3-tert-Butylphenyl N—methyl-N—(2-pyridyl)thiocarbamate |
| 74. | O-3-tert-Butylphenyl N—methyl-N—(3-methyl-2-pyridyl)thiocarbamate |
| 75. | O-3-tert-Butylphenyl N—methyl-N—(4-methyl-2-pyridyl)thiocarbamate |
| 76. | O-3-tert-Butylphenyl N—methyl-N—(5-methyl-2-pyridyl)thiocarbamate |
| 77. | O-3-tert-Butylphenyl N—methyl-N—(6-methyl-2-pyridyl)thiocarbamate |
| 78. | O-3-tert-Butylphenyl N—methyl-N—(4,6-dimethyl-2-pyridyl)thiocarbamate |
| 79. | O-3-tert-Butylphenyl N—methyl-N—(5,6-dimethyl-2-pyridyl)thiocarbamate |
| 80. | O-3-tert-Butylphenyl N—methyl-N—(6-ethyl-2-pyridyl)thiocarbamate |
| 81. | 4-tert-Butylphenyl N—methyl-N—(6-dimethylamino-2-pyridyl)carbamate |
| 82. | O-3,5-Dimethylphenyl N—(6-methoxy-2-pyridyl)-N—methylthiocarbamate |
| 83. | O-4-Chloro-3-methylphenyl N—(6-methoxy-2-pyridyl)-N—methylthiocarbamate |
| 84. | 4-Chloro-3-methylphenyl N—(6-methoxy-2-pyridyl)-N—methylcarbamate |
| 85. | O-4-(1,1,2-Trimethylpropyl)phenyl N—(6-methoxy-2-pyridyl)-N—methylthiocarbamate |
| 86. | O-4-Chlorophenyl N—(6-methoxy-2-pyridyl)-N—methylthiocarbamate |
| 87. | O-4-Ethyl-3-methylphenyl N—(6-methoxy-2-pyridyl)-N—methylthiocarbamate |
| 88. | 4-Ethyl-3-methylphenyl N—(6-methoxy-2-pyridyl)-N—methylcarbamate |
| 89. | O-4-Acetyl-3-methylphenyl N—(6-methoxy-2-pyridyl)-N—methylthiocarbamate |
| 90. | O-5-Isopropyl-2-methylphenyl N—(6-methoxy-2-pyridyl)-N—methylthiocarbamate |
| 91. | O-4-Isobutylphenyl N—(6-methoxy-2-pyridyl)-N—methylthiocarbamate |
| 92. | O-4-Isopropyl-3-methylphenyl N—(6-methoxy-2-pyridyl)-N—methylthiocarbamate |
| 93. | 4-Isopropyl-3-methylphenyl N—(6-methoxy-2-pyridyl)-N—methylcarbamate |
| 94. | O-4-tert-Butyl-3-methylphenyl N—(6-methoxy-2-pyridyl)-N—methylthiocarbamate |
| 95. | 4-tert-Butyl-3-methylphenyl N—(6-methoxy-2-pyridyl)-N—methylcarbamate |
| 96. | O-4-Trifluoromethylphenyl N—(6-methoxy-2-pyridyl)-N—methylthiocarbamate |

-continued

| NO. | THE COMPOUNDS OF THE PRESENT INVENTION |
|---|---|
| 97. | 4-Trifluoromethylphenyl N—(6-methoxy-2-pyridyl)-N—methylcarbamate |
| 98. | 0-4-Nitrophenyl N—(6-methoxy-2-pyridyl)-N—methylthiocarbamate |
| 99. | 0-3-Chloro-4-methylphenyl N—(6-methoxy-2-pyridyl)-N—methylthiocarbamate |
| 100. | 3-Chloro-4-methylphenyl N—(6-methoxy-2-pyridyl)-N—methylcarbamate |
| 101. | 0-4-Bromo-3-methylphenyl N—(6-methoxy-2-pyridyl)-N—methylthiocarbamate |
| 102. | 4-Bromo-3-methylphenyl N—(6-methoxy-2-pyridyl)-N—methylcarbamate |
| 103. | 0-5,6,7,8-Tetrahydro-2-naphthyl N—(6-chloro-4-pyrimidyl)-N—methylthiocarbamate |
| 104. | 0-4-tert-Butylphenyl N—(6-chloro-4-pyrimidyl)-N—methylthiocarbamate |
| 105. | 0-5,6,7,8-Tetrahydro-2-naphthyl N—(6-chloro-2-methylthio-4-pyrimidyl)-N—methyl-thiocarbamate |
| 106. | 0-3-Trifluoromethylphenyl N—(6-methoxy-2-pyridyl)-N—methylthiocarbamate |
| 107. | 3-Trifluoromethylphenyl N—(6-methoxy-2-pyridyl)-N—methylcarbamate |
| 108. | 0-3-Isopropylphenyl N—(6-methoxy-2-pyridyl)-N—methylthiocarbamate |
| 109. | 0-3-Chlorophenyl N—(6-methoxy-2-pyridyl)-N—methylthiocarbamate |
| 110. | 0-3-Bromophenyl N—(6-methoxy-2-pyridyl)-N—methylthiocarbamate |
| 111. | 3-Bromophenyl N—(6-methoxy-2-pyridyl)-N—methylcarbamate |
| 112. | 1,4-Ethano-1,2,3,4-tetrahydro-6-naphthyl N—(6-bromo-2-pyridyl)-N—methylcarbamate |
| 113. | 0-3,4-Dichlorophenyl N—(6-methoxy-2-pyridyl)-N—methylthiocarbamate |
| 114. | 0-4-Chloro-3-methylphenyl N—methyl-N—(6-methyl-2-pyridyl)thiocarbamate |
| 115. | 0-3,4-Dimethylphenyl N—methyl-N—(4-methyl-2-pyridyl)thiocarbamate |
| 116. | 0-2-Methylphenyl N—(6-methoxy-2-pyridyl)-N—methylthiocarbamate |
| 117. | 0-4-Methylphenyl N—(6-methoxy-2-pyridyl)-N—methylthiocarbamate |
| 118. | 4-Chloro-3-methoxyphenol N—(6-methoxy-2-pyridyl)-N—methylcarbamate |
| 119. | 0-4-Chloro-3-methoxyphenyl N—(6-methoxy-2-pyridyl)-N—methylthiocarbamate |
| 120. | 3-Allyloxy-4-chlorophenyl N—(6-methoxy-2-pyridyl)-N—methylcarbamate |
| 121. | 0-3-Allyloxy-4-chlorophenyl N—(6-methoxy-2-pyridyl)-N—methylthiocarbamate |
| 122. | 4-Chloro-3-(2-propynyloxy)phenyl N—(6-methoxy-2-pyridyl)-N—methylcarbamate |
| 123. | 4-Hydroxymethylphenyl N—(6-methoxy-2-pyridyl)-N—methylcarbamate |
| 124. | 4-Acetylphenyl N—(6-methoxy-2-pyridyl)-N—methylcarbamate |
| 125. | 0-4-Isopropenylphenyl N—(6-methoxy-2-pyridyl)-N—methylthiocarbamate |
| 126. | 0-4-Cyanophenyl N—(6-methoxy-2-pyridyl)-N—methylthiocarbamate |
| 127. | 0-4-tert-Butylphenyl N—(2-chloro-4-pyrimidyl)-N—methylthiocarbamate |
| 128. | 0-4-tert-Butylphenyl N—methyl-N—(6-methylamino-5-nitro-2-pyridyl)thiocarbamate |
| 129. | 0-3-tert-Butylphenyl N—methyl-N—(6-methylamino-5-nitro-2-pyridyl)thiocarbamate |
| 130. | 0-5,6,7,8-Tetrahydro-2-naphthyl N—methyl N—(6-methylamino-5-nitro-2-pyridyl)-thiocarbamate |
| 131. | 0-3-tert-Butylphenyl N—methyl-N—(6-dimethylamino-2-pyridyl)thiocarbamate |
| 132. | 0-4-tert-Butylphenyl N—methyl-N—(6-methylamino-2-pyridyl)thiocarbamate |
| 133. | 0-3-tert-Butylphenyl N—methyl-N—(6-methylamino-2-pyridyl)thiocarbamate |
| 134. | 3-Methoxyphenyl N—(6-methoxy-2-pyridyl)-N—methylcarbamate |
| 135. | 0-3-Methoxyphenyl N—(6-methoxy-2-pyridyl)-N—methylthiocarbamate |
| 136. | 4-Methoxyphenyl N—(6-methoxy-2-pyridyl)-N—methylcarbamate |
| 137. | 0-4-Methoxyphenyl N—(6-methoxy-2-pyridyl)-N—methylthiocarbamate |
| 138. | 3-Ethoxyphenyl-N—(6-methoxy-2-pyridyl)-N—methylcarbamate |
| 139. | 0-3-Ethoxyphenyl N—(6-methoxy-2-pyridyl)-N—methylthiocarbamate |
| 140. | 4-Ethoxyphenyl N—(6-methoxy-2-pyridyl)-N—methylcarbamate |
| 141. | 0-4-Ethoxyphenyl N—(6-methoxy-2-pyridyl)-N—methylthiocarbamate |
| 142. | 3-Butoxyphenyl N—(6-methoxy-2-pyridyl)-N—methylcarbamate |
| 143. | 0-3-Butoxyphenyl N—(6-methoxy-2-pyridyl)-N—methylthiocarbamate |
| 144. | 4-Butoxyphenyl N—(6-methoxy-2-pyridyl)-N—methylcarbamate |
| 145. | 0-4-Butoxyphenyl N—(6-methoxy-2-pyridyl)-N—methylthiocarbamate |
| 146. | 0-4-(1-Hydroxyethyl)phenyl N—(6-methoxy-2-pyridyl)-N—methylthiocarbamate |
| 147. | 0-3-tert-Butylphenyl N—(6-ethoxy-2-pyridyl)-N—methylthiocarbamate |
| 148. | 0-4-Methylthiophenyl N—(6-methoxy-2-pyridyl)-N—methylthiocarbamate |
| 149. | 0-3,4-Methylenedioxyphenyl N—(6-methoxy-2-pyridyl)-N—methylthiocarbamate |
| 150. | 0-4-Chloro-3-methylphenyl N—methyl-N—(2-pyridyl)thiocarbamate |
| 151. | 0-4-Chloro-3-methylphenyl N—methyl-N—(5-methyl-2-pyridyl)thiocarbamate |
| 152. | 0-4-Chloro-3-methylphenyl N—methyl-N—(3-methyl-2-pyridyl)thiocarbamate |
| 153. | 0-4-Chloro-3-methylphenyl N—(6-ethyl-2-pyridyl)-N—methylthiocarbamate |
| 154. | 0-4-Chloro-3-methylphenyl N—methyl-N—(5,6-dimethyl-2-pyridyl)thiocarbamate |
| 155. | 0-4-Chloro-3-methylphenyl N—methyl-N—(4,6-dimethyl-2-pyridyl)thiocarbamate |
| 156. | 0-4-Chloro-3-methylphenyl N—(6-chloro-2-pyridyl)-N—methylthiocarbamate |
| 157. | 0-4-Chloro-3-methylphenyl N—methyl-N—(6-dimethylamino-2-pyridyl)thiocarbamate |
| 158. | 0-4-Chloro-3-methylphenyl N—ethyl-N—(6-methoxy-2-pyridyl)thiocarbamate |
| 159. | 0-4-tert-Butylphenyl N—(6-chloro-2-pyridyl)-N—ethylthiocarbamate |
| 160. | 0-3-tert-Butylphenyl N—(6-chloro-2-pyridyl)-N—ethylthiocarbamate |
| 161. | 0-4-tert-Butylphenyl N—ethyl-N—(6-methoxy-2-pyridyl)thiocarbamate |
| 162. | 0-3-tert-Butylphenyl N—ethyl-N—(6-methoxy-2-pyridyl)thiocarbamate |
| 163. | 0-5,6,7,8-Tetrahydro-2-naphthyl N—ethyl-N—(6-methoxy-2-pyridyl)thiocarbamate |
| 164. | 0-3-tert-Butylphenyl N—(6-chloro-2-pyridyl)-N—propylthiocarbamate |
| 165. | 0-4-tert-Butylphenyl N—(6-methoxy-2-pyridyl)-N—propylthiocarbamate |
| 166. | 0-3-tert-Butylphenyl N—(6-methoxy-2-pyridyl)-N—propylthiocarbamate |
| 167. | 0-5,6,7,8-Tetrahydro-2-naphthyl N—(6-methoxy-2-pyridyl)-N—propylthiocarbamate |
| 168. | 0-4-tert-Butylphenyl N—13 isopropyl-N—(6-methoxy-2-pyridyl)thiocarbamate |
| 169. | 0-3-tert-Butylphenyl N—isopropyl-N—(6-methoxy-2-pyridyl)thiocarbamate |
| 170. | 0-5,6,7,8-Tetrahydro-2-naphthyl N—isopropyl-N—(6-methoxy-2-pyridyl)thiocarbamate |
| 171. | 4-Propylphenyl N—(6-methoxy-2-pyridyl)-N—methylcarbamate |
| 172. | 0-4-Propylphenyl N—(6-methoxy-2-pyridyl)-N—methylthiocarbamate |
| 173. | 3-Methyl-4-nitrophenyl N—(6-methoxy-2-pyridyl)-N—methylcarbamate |
| 174. | 0-3-Methyl-4-nitrophenyl N—(6-methoxy-2-pyridyl)-N—methylthiocarbamate |
| 175. | 0-3-Methyl-4-methylthiophenyl N—(6-methoxy-2-pyridyl)-N—methylthiocarbamate |

-continued

| NO. | THE COMPOUNDS OF THE PRESENT INVENTION |
|---|---|
| 176. | O-4-Trifluoromethylphenyl N—methyl-N—(2-pyridyl)thiocarbamate |
| 177. | O-4-Trifluoromethylphenyl N—methyl-N—(6-methyl-2-pyridyl)thiocarbamate |
| 178. | O-4-Trifluoromethylphenyl N—methyl-N—(5-methyl-2-pyridyl)thiocarbamate |
| 179. | O-4-Trifluoromethylphenyl N—methyl-N—(4-methyl-2-pyridyl)thiocarbamate |
| 180. | O-4-Trifluoromethylphenyl N—methyl-N—(3-methyl-2-pyridyl)thiocarbamate |
| 181. | O-4-Trifluoromethylphenyl N—methyl-N—(5,6-dimethyl-2-pyridyl)thiocarbamate |
| 182. | O-4-Trifluoromethylphenyl N—methyl N—(4,6-dimethyl-2-pyridyl)thiocarbamate |
| 183. | O-4-Trifluoromethylphenyl N—(6-ethyl-2-pyridyl)-N—methylthiocarbamate |
| 184. | O-4-Trifluoromethylphenyl N—(6-chloro-2-pyridyl)-N—methylthiocarbamate |
| 185. | O-4-Trifluoromethylphenyl N—(6-bromo-2-pyridyl)-N—methylthiocarbamate |
| 186. | O-4-Trifluoromethylphenyl N—methyl-N—(6-dimethylamino-2-pyridyl)thiocarbamate |
| 187. | O-4-Chloro-3-methylphenyl N—(6-bromo-2-pyridyl)-N—methylthiocarbamate |
| 188. | O-3-Dimethylaminophenyl N—(6-methoxy-2-pyridyl)-N—methylthiocarbamate |
| 189. | 3-Dimethylaminophenyl N—(6-methoxy-2-pyridyl)-N—methylcarbamate |
| 190. | 4-Formylphenyl N—(6-methoxy-2-pyridyl)-N—methylcarbamate |
| 191. | O-4-(1-Bromoethyl)phenyl N—(6-methoxy-2-pyridyl)-N— methylthiocarbamate |
| 192. | O-4-Trifluoromethylphenyl N—ethyl-N—(6-methoxy-2-pyridyl)thiocarbamate |
| 193. | O-4-Ethylphenyl N—ethyl-N—(6-methoxy-2-pyridyl)thiocarbamate |
| 194. | O-4-Isopropylphenyl N—ethyl-N—(6-methoxy-2-pyridyl)thiocarbamate |
| 195. | O-5-Indanyl N—ethyl-N—(6-methoxy-2-pyridyl)thiocarbamate |
| 196. | O-1,4-Methano-1,2,3,4-tetrahydro-6-naphthyl N—ethyl-N—(6-methoxy-2-pyridyl)-thiocarbamate |
| 197. | O-5,6,7,8-Tetrahydro-2-naphthyl N—ethyl-N—(2-pyridyl)thiocarbamate |
| 198. | O-5,6,7,8-Tetrahydro-2-naphthyl N—ethyl-N—(6-methyl-2-pyridyl)thiocarbamate |
| 199. | O-5,6,7,8-Tetrahydro-2-naphthyl N—(6-bromo-2-pyridyl)-N—ethylthiocarbamate |
| 200. | 5,6,7,8-Tetrahydro-2-naphthyl N—ethyl-N—(6-methoxy-2-pyridyl)carbamate |
| 201. | O-4-Methoxymethylphenyl N—(6-methoxy-2-pyridyl)-N—methylthiocarbamate |
| 202. | O-4-Butylphenyl N—(6-methoxy-2-pyridyl)-N—methylthiocarbamate |
| 203. | O-2-Quinolyl N—(6-methoxy-2-pyridyl)-N—methylthiocarbamate |

TABLE 1

| No. of the compound of the present invention | Physical properties and elemental analysis | | | | | |
|---|---|---|---|---|---|---|
| | Melting point (°C.) | IR spectrum (cm$^{-1}$, KBr) | NMR spectrum ($\delta$ = ppm, CDCl$_3$) | Elemental analysis (%) Found value (Calculated value) | | |
| | | | | C | H | N |
| 1 | 91–92.5 | 1335 1415 1460 1575 1715 | 2.46(3H, s) 3.57(3H, s) 6.73–7.93(10H, m) | 73.89 (73.95) | 5.39 (5.51) | 9.71 (9.58) |
| 2 | 92.5–94.5 | 1350 1450 1570 1715 | 2.36(3H, s) 3.40(3H, s) 6.97–7.90(9H, m) 8.32(1H, d) | 73.71 (73.95) | 5.61 (5.51) | 9.19 (9.58) |
| 3 | 149.5–150.5 | 1300 1365 1440 1595 | 2.52(3H, s) 3.73(3H, s) 6.90–7.96(10H, m) | 69.89 (70.10) | 5.19 (5.22) | 8.89 (9.08) |
| 4 | 107–108.5 | 1295 1380 1405 1480 1600 | 2.31(3H, s) 3.73(3H, s) 6.97(1H, d) 7.10–7.95(8H, m) 8.36(1H, d) | 69.91 (70.10) | 5.05 (5.22) | 9.21 (9.08) |
| 5 | 140–141 | 1300 1370 1440 1480 1595 | 2.02(2H, mc) 2.52(3H, s) 2.85(4H, t) 3.71(3H, s) 6.65–7.80(6H, m) | 68.77 (68.43) | 6.10 (6.06) | 9.45 (9.39) |
| 6 | 137.5–139 | 1300 1375 1440 1480 1595 | 1.72(4H, mc) 2.51(3H, s) 2.70(4H, mc) 3.70(3H, s) 6.63–7.76(6H, m) | 69.50 (69.28) | 6.51 (6.46) | 9.06 (8.98) |
| 7 | 123–124.5 | 1300 1380 1440 1480 1575 | 2.03(2H, mc) 8.30(1H, bs) 2.30(3H, s) 2.85(4H, t) 3.70(3H, s) 6.65–7.66(5H, m) | 68.40 (68.43) | 6.14 (6.08) | 9.48 (9.39) |
| 8 | 118.5–119 | 1300 1380 1445 1480 1575 | 1.72(4H, mc) 8.30(1H, bs) 2.30(3H, s) 2.70(4H, mc) 3.68(3H, s) 6.65–7.70(5H, m) | 69.41 (69.28) | 6.43 (6.46) | 8.93 (8.98) |
| 9 | 93.5–95 | 1300 1380 | 2.03(2H, mc) 8.34(1H, d) 2.33(3H, s) | 68.76 (68.43) | 6.09 (6.08) | 9.42 (9.39) |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| | | 1405 | 2.86(4H, t) | | | |
| | | 1480 | 3.70(3H, s) | | | |
| | | 1605 | 6.66–7.37(5H, m) | | | |
| 10 | 98–99.5 | 1300 1605 1375 1400 1440 1480 | 1.72(4H, mc) 8.32(1H, d) 2.32(3H, s) 2.70(4H, mc) 3.68(3H, s) 6.62–7.38(5H, m) | 68.97 (69.28) | 6.51 (6.46) | 9.02 (8.98) |
| 11 | 113–114 | 1290 1380 1415 1480 1575 | 2.00(2H, mc) 6.60–7.34(4H, m) 2.33(3H, s) 7.57(1H, d) 2.81(4H, t) 8.35(1H, d) 3.53(0.7H, s) 3.62(2.3H, s) | 68.81 (68.43) | 6.11 (6.08) | 9.31 (9.39) |
| 12 | 92.5–93.5 | 1285 1380 1420 1490 1575 | 1.73(4H, mc) 6.55–7.33(4H, m) 2.33(3H, s) 7.57(1H, d) 2.68(4H, mc) 8.35(1H, d) 3.53(0.7H, s) 3.63(2.3H, s) | 69.36 (69.28) | 6.51 (6.46) | 8.93 (8.98) |
| 13 | 95–96 | 1370 1420 1465 1605 | 2.04(2H, p) 2.87(4H, t) 3.73(3H, s) 3.89(3H, s) 6.46–7.75(6H, m) | 65.25 (64.95) | 5.74 (5.77) | 9.10 (8.91) |
| 14 | 98.5–99.5 | 1375 1430 1470 1605 | 1.77(4H, mc) 2.67(4H, mc) 3.70(3H, s) 3.86(3H, s) 6.45–7.73(6H, m) | 65.69 (65.83) | 6.12 (6.14) | 8.77 (8.53) |
| 15 | 91–93 | 1365 1410 1450 1600 | 1.52(6H, mc) 3.39(2H, s) 3.76(3H, s) 3.95(3H, s) 6.57–7.80(6H, m) | 67.14 (67.03) | 5.90 (5.92) | 8.11 (8.23) |
| 16 | 97–98.5 | 1350 1410 1460 1585 1715 | 2.07(2H, p) 2.85(4H, t) 3.55(3H, s) 3.88(3H, s) 6.45–7.75(6H, m) | 68.63 (68.44) | 6.02 (6.08) | 9.24 (9.39) |
| 17 | 94–94.5 | 1345 1410 1465 1585 1718 | 1.80(4H, mc) 2.80(4H, mc) 3.63(3H, s) 3.98(3H, s) 6.45–7.80(6H, m) | 68.95 (67.21) | 6.51 (6.45) | 9.18 (8.97) |
| 18 | 60.5–62 | 1340 1410 1460 1580 1718 | 1.48(6H, mc) 3.35(2H, s) 3.59(3H, s) 3.93(3H, s) 6.35–7.75(6H, m) | 70.69 (70.35) | 6.22 (6.21) | 8.47 (8.63) |
| 19 | 117–119 | 1320 1365 1405 1440 1610 | 2.23(3H, s) 2.47(3H, s) 3.72(3H, s) 6.83(1H, s) 6.99–7.95(8H, m) | 70.91 (70.77) | 5.81 (5.62) | 8.55 (8.68) |
| 20 | 116–117.5 | 1320 1370 1470 1610 | 1.73(4H, mc) 6.65–7.20(5H, m) 2.27(3H, s) 2.46(3H, s) 2.70(4H, mc) 3.67(3H, s) | 69.56 (69.90) | 6.82 (6.79) | 8.65 (8.58) |
| 21 | 128–129 | 1320 1375 1480 1610 | 2.03(2H, mc) 6.68–7.33(5H, m) 2.28(3H, s) 2.48(3H, s) 2.86(4H, t) 3.67(3H, s) | 69.14 (69.28) | 6.41 (6.46) | 9.04 (8.98) |
| 22 | 155.5–156.5 | 1320 1365 1430 1480 1580 | 3.73(3H, s) 7.07–7.96(10H, m) | 62.38 (62.09) | 4.03 (3.98) | 8.73 (8.51) |
| 23 | 126–127.5 | 1300 1360 1420 1460 1575 | 1.69(4H, mc) 2.67(4H, mc) 3.68(3H, s) 6.60–7.80(6H, m) | 61.47 (61.34) | 5.28 (5.15) | 8.34 (8.42) |
| 24 | 70– | 1350 | 1.75(4H, mc) | 64.68 | 5.50 | 8.88 |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| | 71 | 1410<br>1470<br>1580<br>1720 | 2.74(4H, mc)<br>3.58(3H, s)<br>6.60–7.90(6H, m) | (64.46) | (5.41) | (8.84) |
| 25 | 124–125 | 1295<br>1365<br>1420<br>1470<br>1565 | 2.02(2H, p)<br>2.84(4H, t)<br>3.71(3H, s)<br>6.50–7.80(6H, m) | 60.55<br>(60.28) | 4.80<br>(4.74) | 8.85<br>(8.79) |
| 26 | 94–96 | 1305<br>1380<br>1425<br>1470<br>1585 | 2.03(2H, p)<br>2.86(4H, t)<br>3.73(3H, s)<br>6.67–7.90(6H, m)<br>8.35–8.65(1H, m) | 67.36<br>(67.58) | 5.76<br>(5.67) | 9.95<br>(9.85) |
| 27 | 119.5–121 | 1300<br>1370<br>1420<br>1465<br>1585 | 1.71(4H, mc)<br>2.70(4H, mc)<br>3.72(3H, s)<br>6.65–7.87(6H, m)<br>8.32–8.60(1H, m) | 68.29<br>(68.43) | 6.06<br>(6.08) | 9.35<br>(9.39) |
| 28 | 87–88 | 1320<br>1370<br>1420<br>1460<br>1595 | 1.28(9H, s)<br>3.71(3H, s)<br>3.90(3H, s)<br>6.50–7.76(7H, m) | 65.55<br>(65.43) | 6.63<br>(6.71) | 8.55<br>(8.48) |
| 29 | 100.5–101 | 1300<br>1375<br>1430<br>1465<br>1585 | 1.28(9H, s)<br>3.73(3H, s)<br>6.80–7.85(7H, m)<br>8.47(1H, d) | 67.84<br>(67.98) | 6.75<br>(6.71) | 9.28<br>(9.33) |
| 30 | 127–128.5 | 1300<br>1370<br>1460<br>1595 | 1.27(9H, s)<br>2.52(3H, s)<br>3.71(3H, s)<br>6.80–7.73(7H, m) | 68.87<br>(68.76) | 7.13<br>(7.05) | 8.86<br>(8.91) |
| 31 | 113–114 | 1305<br>1380<br>1480<br>1580 | 1.28(9H, s)<br>2.32(3H, s)<br>3.70(3H, s)<br>6.78–7.65(6H, m)<br>8.30(1H, bs) | 68.88<br>(68.76) | 7.01<br>(7.05) | 8.94<br>(8.91) |
| 32 | 107–108 | 1290<br>1380<br>1400<br>1480<br>1605 | 1.28(9H, s)<br>2.33(3H, s)<br>3.69(3H, s)<br>6.80–7.48(6H, m)<br>8.30(1H, d) | 69.08<br>(68.76) | 7.03<br>(7.05) | 8.89<br>(8.91) |
| 33 | 118.5–119 | 1290<br>1375<br>1415<br>1475<br>1570 | 1.27(9H, s) 8.26–8.50(1H, m)<br>2.34(3H, s)<br>3.54(0.6H, s)<br>3.63(2.4H, s)<br>6.75–7.73(6H, m) | 68.64<br>(68.76) | 7.12<br>(7.05) | 8.83<br>(8.91) |
| 34 | 126.5–127.5 | 1320<br>1380<br>1405<br>1485<br>1610 | 1.28(9H, s)<br>2.28(3H, s)<br>2.47(3H, s)<br>3.65(3H, s)<br>6.77–7.46(6H, m) | 69.55<br>(69.48) | 7.40<br>(7.37) | 8.45<br>(8.53) |
| 35 | 78–80 | 1300 1710<br>1340<br>1405<br>1460<br>1575 | 1.33(9H, s)<br>3.60(3H, s)<br>3.93(3H, s)<br>6.36–7.73(7H, m) | 69.11<br>(68.77) | 7.09<br>(7.05) | 8.83<br>(8.91) |
| 36 | 113–114.5 | 1320<br>1365<br>1420<br>1460<br>1595 | 0.71(3H, t) 6.56–7.76(7H, m)<br>1.31(6H, s)<br>1.66(2H, q)<br>3.80(3H, s)<br>3.96(3H, s) | 66.39<br>(66.26) | 6.96<br>(7.02) | 8.18<br>(8.13) |
| 37 | 132.5–133.5 | 1290<br>1360<br>1415<br>1460<br>1565 | 1.75(4H, mc)<br>2.74(4H, mc)<br>3.71(3H, s)<br>6.60–7.70(6H, m) | 53.73<br>(54.12) | 4.59<br>(4.54) | 7.38<br>(7.42) |
| 38 | 125–126.5 | 1370<br>1415<br>1455<br>1600 | 1.59(8H, mc)<br>2.96(2H, s)<br>3.76(3H, s)<br>3.93(3H, s)<br>6.50–7.70(6H, m) | 67.47<br>(67.78) | 6.30<br>(6.25) | 7.75<br>(7.90) |
| 39 | 111– | 1320 | 2.22(6H, s) | 63.35 | 6.07 | 9.04 |

TABLE 1-continued

| No. of the compound of the present invention | Physical properties and elemental analysis | | | Elemental analysis (%) Found value (Calculated value) | | |
|---|---|---|---|---|---|---|
| | Melting point (°C.) | IR spectrum (cm$^{-1}$, KBr) | NMR spectrum (δ = ppm, CDCl$_3$) | C | H | N |
| | 112 | 1365<br>1410<br>1455<br>1595 | 3.73(3H, s)<br>3.90(3H, s)<br>6.45–7.23(5H, m)<br>7.55(1H, t) | (63.55) | (6.00) | (9.26) |
| 40 | 91–92 | 1350<br>1410<br>1460<br>1580<br>1715 | 2.20(6H, s)<br>3.56(3H, s)<br>3.90(3H, s)<br>6.50(1H, d)<br>6.70–7.76(5H, m) | 67.32<br>(67.11) | 6.52<br>(6.33) | 9.95<br>(9.78) |
| 41 | 94–95.5 | 1300<br>1370<br>1410<br>1480<br>1600 | 1.23(3H, t) 8.38(1H, d)<br>2.04(2H, mc)<br>2.40–3.15(6H, m)<br>3.72(3H, s)<br>6.66–7.40(5H, m) | 69.15<br>(69.28) | 6.42<br>(6.46) | 9.00<br>(8.98) |
| 42 | 63–64 | 1300<br>1365<br>1410<br>1480<br>1600 | 1.23(3H, t) 8.38(1H, d)<br>1.73(4H, mc)<br>2.40–3.00(6H, m)<br>3.71(3H, s)<br>6.68–7.42(5H, m) | 70.13<br>(69.90) | 6.75<br>(6.79) | 8.67<br>(8.58) |
| 43 | 107–108 | 1300<br>1365<br>1435<br>1595 | 1.32(3H, t)<br>2.83(2H, q)<br>3.77(3H, s)<br>6.93–7.96(10H, m) | 70.92<br>(70.77) | 5.67<br>(5.62) | 8.49<br>(8.68) |
| 44 | 102–103.5 | 1300<br>1370<br>1435<br>1590 | 1.31(3H, t)<br>2.05(2H, mc)<br>2.60–3.10(6H, m)<br>3.73(3H, s)<br>6.68–7.80(6H, m) | 69.40<br>(69.28) | 6.52<br>(6.46) | 9.02<br>(8.98) |
| 45 | 102–103 | 1300<br>1375<br>1445<br>1595 | 1.30(3H, t)<br>1.73(4H, mc)<br>2.50–3.10(6H, m)<br>3.72(3H, s)<br>6.68–7.77(6H, m) | 69.77<br>(69.90) | 6.77<br>(6.79) | 8.61<br>(8.58) |
| 46 | 113–114 | 1300<br>1375<br>1445<br>1475<br>1590 | 1.28(9H, s)<br>1.30(3H, t)<br>2.82(2H, q)<br>3.73(3H, s)<br>6.82–7.76(7H, m) | 69.90<br>(69.48) | 7.33<br>(7.37) | 8.45<br>(8.53) |
| 47 | 108–109 | 1300<br>1355<br>1420<br>1460<br>1580 | 2.13(3H, s)<br>2.41(3H, s)<br>3.71(3H, s)<br>7.01–7.90(9H, m) | 70.92<br>(70.77) | 5.65<br>(5.62) | 9.05<br>(8.68) |
| 48 | 102.5–104 | 1300<br>1360<br>1430<br>1465<br>1580 | 2.02(2H, mc) 6.66–7.56(5H, m)<br>2.23(3H, s)<br>2.46(3H, s)<br>2.86(4H, t)<br>3.68(3H, s) | 69.59<br>(69.28) | 6.52<br>(6.46) | 9.01<br>(8.98) |
| 49 | 98–99.5 | 1300<br>1360<br>1430<br>1460<br>1580 | 1.73(4H, mc) 6.65–7.56(5H, m)<br>2.25(3H, s)<br>2.46(3H, s)<br>2.71(4H, mc)<br>3.68(3H, s) | 70.21<br>(69.90) | 6.76<br>(6.79) | 8.61<br>(8.58) |
| 50 | 150–151.5 | 1305<br>1380<br>1460<br>1580 | 1.28(9H, s)<br>2.24(3H, s)<br>2.46(3H, s)<br>3.70(3H, s)<br>6.80–7.53(6H, m) | 69.57<br>(69.48) | 7.32<br>(7.37) | 8.50<br>(8.53) |
| 51 | 85.5–86.5 | 1320 1595<br>1365<br>1420<br>1460<br>1570 | 1.20(9H, s)<br>3.70(3H, s)<br>3.86(3H, s)<br>6.43–7.71(7H, m) | 65.15<br>(65.43) | 6.69<br>(6.71) | 8.44<br>(8.48) |
| 52 | 81–82 | 1310 1590<br>1350 1720<br>1410<br>1460<br>1575 | 1.31(9H, s)<br>3.58(3H, s)<br>3.90(3H, s)<br>6.33–7.70(7H, m) | 69.05<br>(68.77) | 7.11<br>(7.05) | 8.94<br>(8.91) |
| 53 | 143–144 | 1300<br>1365<br>1425<br>1470<br>1570 | 1.28(9H, s)<br>3.73(3H, s)<br>6.76–7.63(7H, m) | 54.20<br>(53.83) | 5.13<br>(5.05) | 7.48<br>(7.39) |
| 54 | 126.5– | 1300 | 1.23(9H,s) | 60.72 | 5.77 | 8.47 |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| | 128 | 1365 1415 1460 1575 | 3.68(3H, s) 6.73–7.63(7H, m) | (60.98) | (5.72) | (8.37) |
| 55 | 86–87 | 1310 1720 1345 1415 1460 1585 | 0.66(3H, t) 6.33–7.73(7H, m) 1.25(6H, s) 1.60(2H, q) 3.56(3H, s) 3.90(3H, s) | 69.33 (69.49) | 7.34 (7.37) | 8.45 (8.53) |
| 56 | 52–53 | 1320 1365 1415 1460 1590 | 0.81(3H, t) 6.33–7.73(7H, m) 1.20(3H, d) 6.50–7.70(7H, m) 1.56(2H, p) 2.61(1H, sex) 3.75(3H, s) | 65.17 (65.43) | 6.63 (6.71) | 8.55 (8.48) |
| 57 | 74–75 | 1365 1405 1460 1580 1710 | 0.75(3H, t) 3.86(3H, s) 1.15(3H, d) 6.30–7.70(7H, m) 1.51(2H, p) 2.55(1H, sex) 3.51(3H, s) | 69.08 (68.77) | 7.07 (7.05) | 8.94 (8.91) |
| 58 | 55–56 | 1320 1365 1410 1460 1595 | 1.17(6H, d) 2.86(1H, h) 3.69(3H, s) 3.86(3H, s) 6.47–7.85(7H, m) | 64.80 (64.54) | 6.41 (6.37) | 8.83 (8.86) |
| 59 | 64–65 | 1350 1410 1460 1590 1715 | 1.25(6H, d) 2.91(1H, h) 3.60(3H, s) 3.91(3H, s) 6.40–7.85(7H, m) | 68.25 (67.98) | 6.63 (6.71) | 9.16 (9.33) |
| 60 | oil | 1335* 1400 1455 1575 1725 | 1.60(8H, mc) 2.90(2H, s) 3.59(3H, s) 3.92(3H, s) 6.40–7.60(6H, m) | 70.83 (70.99) | 6.61 (6.55) | 8.38 (8.28) |
| 61 | oil | 1320* 1360 1420 1460 1600 | 2.35(3H, s) 3.74(3H, s) 3.92(3H, s) 6.48–7.75(7H, m) | 62.77 (62.49) | 5.91 (5.94) | 9.22 (9.72) |
| 62 | oil | 1320* 1360 1420 1460 1600 | 1.21(3H, t) 2.65(2H, q) 3.71(3H, s) 3.91(3H, s) 6.35–7.75(7H, m) | 63.43 (63.56) | 5.92 (6.00) | 9.14 (9.27) |
| 63 | 69.5–70.5 | 1320 1360 1415 1460 1595 | 1.21(3H, t) 2.60(2H, q) 3.70(3H, s) 3.92(3H, s) 6.43–7.73(7H, m) | 63.70 (63.56) | 5.92 (6.00) | 9.18 (9.27) |
| 64 | 87–88 | 1325 1370 1420 1455 1595 | 3.74(3H, s) 7.63(1H, t) 3.93(3H, s) 6.67(1H, d) 6.85–7.15(3H, m) 7.49(2H, d) | 47.76 (47.60) | 3.69 (3.70) | 7.83 (7.93) |
| 65 | 87–88 | 1350 1405 1455 1570 1705 | 3.50(3H, s) 3.86(3H, s) 6.48(1H, d) 6.86–7.70(6H, m) | 49.77 (49.87) | 3.81 (3.88) | 8.04 (8.30) |
| 66 | 73.5–75 | 1320 1360 1410 1445 1580 | 2.38(6H, s) 6.95(1H, d) 3.74(3H, s) 7.57(1H, t) 3.93(3H, s) 6.62(1H, d) 6.80(2H, s) | 50.49 (50.40) | 4.46 (4.47) | 7.06 (7.34) |
| 67 | 64.5–66 | 1320 1355 1415 1455 1590 | 2.33(6H, s) 7.01(1H, d) 3.75(3H, s) 7.63(1H, t) 3.93(3H, s) 6.68(1H, d) 6.85(2H, s) | 57.03 (57.05) | 5.17 (5.08) | 8.26 (8.31) |
| 68 | oil | 1330* 1410 1440 1570 1710 | 1.48(6H, mc) 3.35(2H, s) 3.57(3H, s) 6.65–6.90(6H, m) | 58.04 (57.92) | 4.60 (4.66) | 7.45 (7.50) |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| 69 | 135–136 | 1300 1500 1360 1415 1460 1555 | 3.00(6H, s) 3.73(3H, s) 6.28(1H, d) 6.65(1H, d) 7.10–7.97(8H, m) | 67.32 (67.62) | 5.58 (5.67) | 12.31 (12.45) |
| 70 | 108–109.5 | 1300 1595 1360 1420 1460 1555 | 1.72(4H, mc) 6.50–7.19(4H, m) 2.69(4H, mc) 7.42(1H, t) 3.02(6H, s) 3.71(3H, s) 6.30(1H, d) | 67.13 (66.83) | 6.69 (6.78) | 12.62 (12.30) |
| 71 | 83–84 | 1300 1595 1360 1415 1465 1555 | 1.97(2H, p) 6.48–7.27(4H, m) 2.80(4H, t) 7.41(1H, t) 2.98(6H, s) 3.66(3H, s) 6.29(1H, d) | 66.34 (66.02) | 6.52 (6.46) | 13.15 (12.83) |
| 72 | 89.5–90.5 | 1375 1420 1475 1555 1595 | 1.31(9H, s) 7.00(2H, d) 3.06(6H, s) 7.20–7.63(3H, m) 3.75(3H, s) 6.37(1H, d) 6.63(1H, d) | 66.56 (66.43) | 7.26 (7.33) | 12.23 (12.23) |
| 73 | 88–89.5 | 1310 1370 1420 1470 1585 | 1.26(9H, s) 3.73(3H, s) 6.71–7.90(7H, m) 8.37–8.62(1H, m) | 67.75 (67.97) | 6.65 (6.71) | 9.43 (9.32) |
| 74 | 65–67.5 | 1290 1375 1415 1480 1575 | 1.26(s) 1.31(s) (9H) 2.36(3H, s) 8.26–8.51(1H, m) 3.56(0.6H, s) 3.65(2.4H, s) 6.65–7.75(6H, m) | 68.58 (68.75) | 7.10 (7.05) | 8.99 (8.91) |
| 75 | 96–98 | 1295 1370 1400 1480 1605 | 1.28(9H, s) 2.35(3H, s) 3.70(3H, s) 6.72–7.45(6H, m) 8.34(1H, d) | 69.02 (68.75) | 6.96 (7.05) | 8.84 (8.91) |
| 76 | 94–95.5 | 1310 1385 1480 1580 | 1.27(9H, s) 2.30(3H, s) 3.71(3H, s) 6.70–7.67(6H, m) 8.32(1H, bs) | 68.43 (68.75) | 7.03 (7.05) | 8.97 (8.91) |
| 77 | 116–117.5 | 1305 1370 1440 1480 1595 | 1.27(9H, s) 2.53(3H, s) 3.71(3H, s) 6.70–7.75(7H, m) | 68.46 (68.75) | 6.99 (7.05) | 9.00 (8.91) |
| 78 | 76–77 | 1325 1385 1480 1610 | 1.28(9H, s) 2.30(3H, 2) 2.49(3H, s) 3.69(3H, s) 6.72–7.45(6H, m) | 69.84 (69.48) | 7.37 (7.36) | 8.59 (8.53) |
| 79 | 98–99 | 1300 1360 1450 1580 | 1.28(9H, s) 2.27(3H, s) 2.48(3H, s) 3.70(3H, s) 6.70–7.56(6H, m) | 69.73 (69.48) | 7.44 (7.36) | 8.60 (8.53) |
| 80 | 104.4–106 | 1300 1380 1440 1480 1595 | 1.28(9H, s) 1.31(3H, t) 2.82(2H, q) 3.73(3H, s) 6.70–7.80(7H, m) | 69.26 (69.48) | 7.32 (7.36) | 8.61 (8.53) |
| 81 | 68–69 | 1340 1715 1405 1500 1560 1590 | 1.28(9H, s) 3.02(6H, s) 3.53(3H, s) 6.22(1H, d) 6.85–7.60(6H, m) | 69.37 (69.69) | 7.54 (7.69) | 12.95 (12.83) |
| 82 | 64–65 | 1320 1370 1415 1460 1595 | 2.30(6H, s) 3.75(3H, s) 3.92(3H, s) 6.50–7.12(5H, m) 7.58(1H, t) | 63.51 (63.55) | 6.15 (6.00) | 9.55 (9.26) |
| 83 | 93–94 | 1325 1370 1415 1460 | 2.35(3H, s) 7.66 (1H, t) 3.76(3H, s) 3.95(3H, s) 6.56–7.16(4H, m) | 56.06 (55.81) | 4.52 (4.68) | (8.67) |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| 84 | 107–108 | 1600 1345 1405 1455 1575 1710 | 7.35(1H, d) 2.34(3H, s) 3.57(3H, s) 3.92(3H, s) 6.51(1H, d) 6.75–7.73(5H, m) | 59.02 (58.73) | 4.95 (4.92) | 9.06 (9.13) |
| 85 | 107.5–109 | 1320 1370 1420 1460 1595 | 0.74(6H, d) 6.62(1H, d) 1.24(6H, s) 6.80–7.12(3H, m) 1.93(1H, h) 7.30(2H, d) 3.75(3H, s) 7.58(1H, t) 3.93(3H, s) | 66.91 (67.00) | 7.35 (7.31) | 7.98 (7.81) |
| 86 | 68–69 | 1325 1370 1415 1485 1590 | 3.75(3H, s) 7.71(1H, t) 3.95((3H, s) 6.71(1H, d) 6.88–7.20(3H, m) 7.38(2H, d) | 54.33 (54.45) | 4.29 (4.24) | 8.93 (9.07) |
| 87 | 83–85 | 1315 1360 1405 1450 1590 | 1.18(3H, t) 6.50–7.27(5H, m) 2.27(3H, s) 7.56(1H, t) 2.59(2H, q) 3.75(3H, s) 3.92(3H, s) | 64.52 (64.53) | 6.45 (6.37) | 8.68 (8.85) |
| 88 | 61–62 | 1350 1415 1465 1585 1720 | 1.18(3H, t) 6.48(1H, d) 2.28(3H, s) 6.75–7.77(5H, m) 2.59(2H, q) 3.57(3H, s) 3.91(3H, s) | 67.92 (67.98) | 6.63 (6.71) | 9.20 (9.32) |
| 89 | 93–94 | 1315 1590 1360 1680 1405 1445 1560 | 2.54(6H, s) 3.73(3H, s) 3.91(3H, s) 6.63(1H, d) 6.85–7.86(5H, m) | 61.91 (61.79) | 5.56 (5.49) | 8.53 (8.47) |
| 90 | oil | 1330* 1370 1425 1470 1605 | 1.20(6H, d) 6.58(1H, d) 2.16(3H, s) 6.75–7.25(4H, m) 2.84(1H, h) 7.55(1H, t) 3.70(3H, s) 3.87(3H, s) | 65.47 (65.42) | 6.68 (6.71) | 8.18 (8.47) |
| 91 | 80–81.5 | 1320 1365 1420 1460 1595 | 0.88(6H, d) 1.45–2.23(1H, m) 2.46(2H, d) 6.62(1H, d) 3.75(3H, s) 6.78–7.26(5H, m) 3.92(3H, s) 7.58(1H, t) | 65.69 (65.42) | 6.82 (6.71) | 8.23 (8.47) |
| 92 | 67–68 | 1315 1350 1400 1440 1590 | 1.21(6H, d) 6.65(1H, d) 2.32(3H, s) 6.80–7.40(4H, m) 3.12(1H, h) 7.55(1H, t) 3.76(3H, s) 3.94(3H, s) | 65.25 (65.42) | 6.57 (6.71) | 8.29 (8.47) |
| 93 | 88–89 | 1340 1410 1460 1580 1715 | 1.21(6H, d) 6.48(1H, d) 2.33(3H, s) 6.76–7.73(5H, m) 3.12(1H, h) 3.60(3H, s) 3.93(3H, s) | 68.72 (68.76) | 6.91 (7.05) | 8.91 (8.91) |
| 94 | 97–98 | 1320 1360 1420 1455 1590 | 1.40(9H, s) 6.73–7.12(3H, m) 2.51(3H, s) 7.35(1H, d) 3.75(3H, s) 7.58(1H, t) 3.92(3H, s) 6.63(1H, d) | 66.24 (66.24) | 6.98 (7.02) | 8.25 (8.13) |
| 95 | 93–94.5 | 1345 1405 1455 1580 1710 | 1.40(9H, s) 6.92(2H, bs) 2.53(3H, s) 7.16–7.68(3H, m) 3.59(3H, s) 3.92(3H, s) 6.48(1H, d) | 69.36 (69.48) | 7.36 (7.36) | 8.73 (8.53) |
| 96 | 81–82 | 1325 1375 1410 1460 1600 | 3.75(3H, s) 7.60(1H, t) 3.93(3H, s) 7.62(2H, d) 6.65(1H, d) 6.95(1H, d) 7.17(2H, d) | 52.48 (52.62) | 3.99 (3.82) | 8.09 (8.18) |
| 97 | 85–86 | 1320 1415 1470 1580 1715 | 3.58(3H, s) 3.92(3H, s) 6.52(1H, d) 7.15–7.80(6H, m) | 55.21 (55.21) | 4.21 (4.01) | 8.87 (8.58) |
| 98 | 91–92.5 | 1340 1480 1375 1605 1405 | 3.76(3H, s) 7.67(1H, t) 3.93(3H, s) 8.26(2H, d) 6.71(1H, d) | 52.73 (52.65) | 4.09 (4.10) | 12.98 (13.15) |

TABLE 1-continued

| No. of the compound of the present invention | Physical properties and elemental analysis ||||||
|---|---|---|---|---|---|
| | Melting point (°C.) | IR spectrum (cm$^{-1}$, KBr) | NMR spectrum (δ = ppm, CDCl$_3$) | Elemental analysis (%) Found value (Calculated value) |||
| | | | | C | H | N |
| | | 1425 | 6.98(1H, d) | | | |
| | | 1460 | 7.25(2H, d) | | | |
| 99 | 103–105 | 1325 | 2.32(3H, s) 7.58(1H, t) | 55.80 | 4.56 | 8.57 |
| | | 1365 | 3.73(3H, s) | (55.81) | (4.68) | (8.67) |
| | | 1410 | 3.92(3H, s) | | | |
| | | 1460 | 6.63(1H, d) | | | |
| | | 1600 | 6.75–7.33(4H, m) | | | |
| 100 | 114.5–115.5 | 1350 | 2.33(3H, s) | 58.59 | 4.80 | 8.40 |
| | | 1410 | 3.56(3H, s) | (58.73) | (4.92) | (9.13) |
| | | 1460 | 3.91(3H, s) | | | |
| | | 1580 | 6.50(1H, d) | | | |
| | | 1715 | 6.83–7.73(5H, m) | | | |
| 101 | 105.5–107 | 1320 | 2.35(3H, s) | 49.03 | 4.21 | 7.43 |
| | | 1365 | 3.73(3H, s) | (49.05) | (4.11) | (7.62) |
| | | 1410 | 3.91(3H, s) | | | |
| | | 1455 | 6.53–7.10(4H, m) | | | |
| | | 1600 | 7.20–7.80(2H, m) | | | |
| 102 | 110–110.5 | 1355 | 2.38(3H, s) | 51.03 | 4.34 | 8.11 |
| | | 1415 | 3.56(3H, s) | (51.29) | (4.30) | (7.97) |
| | | 1460 | 3.92(3H, s) | | | |
| | | 1580 | 6.50(1H, d) | | | |
| | | 1720 | 6.70–7.72(5H, m) | | | |
| 103 | 88.5–90 | 1355 | 1.78(4H, mc) 8.85(1H, s) | 57.83 | 4.99 | 12.21 |
| | | 1420 | 2.76(4H, mc) | (57.56) | (4.83) | (12.58) |
| | | 1445 | 3.82(3H, s) | | | |
| | | 1490 | 6.65–7.20(3H, m) | | | |
| | | 1560 | 7.73(1H, s) | | | |
| 104 | oil | 1350* | 1.35(9H, s) 8.90(1H, s) | 57.06 | 5.42 | 12.73 |
| | | 1420 | 3.86(3H, s) | (57.22) | (5.40) | (12.51) |
| | | 1445 | 7.00(2H, d) | | | |
| | | 1500 | 7.46(2H, d) | | | |
| | | 1560 | 7.78(1H, s) | | | |
| 105 | 110–111 | 1335 1525 | 1.73(4H, mc) | 53.69 | 4.81 | 10.78 |
| | | 1380 | 2.51(3H, s) | (53.74) | (4.77) | (11.06) |
| | | 1425 | 2.72(4H, mc) | | | |
| | | 1460 | 3.76(3H, s) | | | |
| | | 1485 | 6.60–7.30(4H, m) | | | |
| 106 | 71–72 | 1315 | 3.75(3H, s) | 52.50 | 4.01 | 7.82 |
| | | 1370 | 3.92(3H, s) | (52.62) | (3.82) | (8.18) |
| | | 1420 | 6.65(1H, d) | | | |
| | | 1460 | 6.97(1H, d) | | | |
| | | 1590 | 7.15–7.78(5H, m) | | | |
| 107 | 79–80 | 1320 | 3.60(3H, s) | 55.39 | 3.91 | 8.22 |
| | | 1410 | 3.93(3H, s) | (55.21) | (4.01) | (8.58) |
| | | 1445 | 6.55(1H, d) | | | |
| | | 1580 | 7.20–7.87(6H, m) | | | |
| | | 1720 | | | | |
| 108 | 50–51 | 1320 1595 | 1.23(6H, d) 6.75–7.41(5H, m) | 64.84 | 6.19 | 8.55 |
| | | 1360 | 2.92(1H, h) 7.60(1H, t) | (64.53) | (6.37) | (8.85) |
| | | 1410 | 3.75(3H, s) | | | |
| | | 1455 | 3.94(3H, s) | | | |
| | | 1570 | 6.61(1H, d) | | | |
| 109 | 58.5– | 1320 | 3.73(3H, s) | 54.38 | 4.16 | 8.73 |
| | | 1360 | 3.91(3H, s) | (54.45) | (4.24) | (9.07) |
| | | 1420 | 6.64(1H, d) | | | |
| | | 1460 | 6.85–7.37(5H, m) | | | |
| | | 1580 | 7.58(1H, t) | | | |
| 110 | 69–69.5 | 1335 | 3.73(3H, s) | 47.47 | 3.79 | 7.73 |
| | | 1380 | 3.92(3H, s) | (47.60) | (3.70) | (7.93) |
| | | 1425 | 6.63(1H, d) | | | |
| | | 1460 | 6.82–7.40(5H, m) | | | |
| | | 1570 | 7.60(1H, t) | | | |
| 111 | 103–103.5 | 1360 | 3.57(3H, s) | 49.93 | 3.99 | 8.19 |
| | | 1410 | 3.93(3H, s) | (49.87) | (3.88) | (8.30) |
| | | 1460 | 6.53(1H, d) | | | |
| | | 1580 | 7.03–7.70(6H, m) | | | |
| | | 1715 | | | | |
| 112 | oil | 1340* | 1.56(8H, mc) | 59.05 | 5.02 | 7.14 |
| | | 1415 | 2.99(2H, s) | (58.93) | (4.94) | (7.23) |
| | | 1445 | 3.62(3H, s) | | | |
| | | 1580 | 6.85–7.95(6H, m) | | | |
| | | 1730 | | | | |
| 113 | 78–79 | 1320 | 3.73(3H, s) | 49.16 | 3.33 | 7.88 |
| | | 1370 | 3.92(3H, s) | (48.99) | (3.52) | (8.16) |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| | | 1415 | 6.56–7.80(6H, m) | | | |
| | | 1455 | | | | |
| | | 1595 | | | | |
| 114 | 134– | 1300 | 2.34(3H, s) | 58.79 | 4.88 | 9.05 |
| | 136 | 1370 | 2.57(3H, s) | (58.72) | (4.92) | (9.13) |
| | | 1440 | 3.75(3H, s) | | | |
| | | 1465 | 6.70–7.80(6H, m) | | | |
| | | 1590 | | | | |
| 115 | 113– | 1295 | 2.23(6H, s) | 66.98 | 6.29 | 10.00 |
| | 114 | 1370 | 2.37(3H, s) | (67.10) | (6.33) | (9.78) |
| | | 1400 | 3.73(3H, s) | | | |
| | | 1475 | 6.70–7.36(5H, m) | | | |
| | | 1600 | 8.34(1H, d) | | | |
| 116 | oil | 1320* | 2.18(3H, s) 7.52(1H, t) | 62.27 | 5.66 | 9.83 |
| | | 1360 | 3.71(3H, s) | (62.47) | (5.59) | (9.71) |
| | | 1415 | 3.87(3H, s) | | | |
| | | 1460 | 6.60(1H, d) | | | |
| | | 1600 | 6.80–7.30(5H, m) | | | |
| 117 | 66.5– | 1320 | 2.27(3H, s) 7.53(1H, t) | 62.13 | 5.51 | 9.87 |
| | 67.5 | 1370 | 3.72(3H, s) | (62.47) | (5.59) | (9.71) |
| | | 1415 | 3.88(3H, s) | | | |
| | | 1460 | 6.60(1H, d) | | | |
| | | 1595 | 6.80–7.30(5H, m) | | | |
| 118 | 89– | 1345 | 3.57(3H, s) | 55.53 | 4.56 | 8.44 |
| | 90 | 1410 | 3.85(3H, s) | (55.82) | (4.68) | (8.67) |
| | | 1460 | 3.92(3H, s) | | | |
| | | 1595 | 6.40–6.90(3H, m) | | | |
| | | 1720 | 7.17–7.73(3H, m) | | | |
| 119 | 64.5– | 1325 | 3.76(3H, s) | 53.13 | 4.29 | 8.12 |
| | 65.5 | 1365 | 3.88(3H, s) | (53.17) | (4.46) | (8.26) |
| | | 1420 | 3.94(3H, s) | | | |
| | | 1460 | 6.50–7.80(6H, m) | | | |
| | | 1595 | | | | |
| 120 | 78– | 1340 | 3.56(3H, s) | 58.52 | 4.94 | 7.80 |
| | 79 | 1410 | 3.91(3H, s) | (58.54) | (4.91) | (8.03) |
| | | 1460 | 4.56(2H, mc) | | | |
| | | 1580 | 5.08–6.91(6H, m) | | | |
| | | 1715 | 7.11–7.71(3H, m) | | | |
| 121 | 116.5– | 1315 | 3.71(3H, s) | 55.89 | 4.75 | 7.50 |
| | 117.5 | 1375 | 3.90(3H, s) | (55.96) | (4.69) | (7.67) |
| | | 1415 | 4.55(2H, mc) | | | |
| | | 1460 | 5.01–7.43(8H, m) | | | |
| | | 1590 | 7.60(1H, t) | | | |
| 122 | 79.5– | 1305 1730 | 2.55(1H, t) 6.66–7.81(5H, m) | 58.97 | 4.54 | 8.04 |
| | 80.5 | 1355 | 3.58(3H, s) | (58.88) | (4.36) | (8.07) |
| | | 1410 | 3.91(3H, s) | | | |
| | | 1460 | 4.75(2H, d) | | | |
| | | 1575 | 6.55(1H, d) | | | |
| 123 | 94.5– | 1340 3500 | 2.50(1H, bt) 6.95–7.75(6H, m) | 62.48 | 5.71 | 9.60 |
| | 95.5 | 1405 | 3.57(3H, s) | (62.49) | (5.59) | (9.71) |
| | | 1455 | 3.90(3H, s) | | | |
| | | 1580 | 4.58(2H, bd) | | | |
| | | 1710 | 6.50(1H, d) | | | |
| 124 | 112– | 1400 | 2.59(3H, s) 8.03(2H, d) | 64.02 | 5.50 | 9.18 |
| | 112.5 | 1460 | 3.61(3H, s) | (63.99) | (5.37) | (9.32) |
| | | 1570 | 3.94(3H, s) | | | |
| | | 1665 | 6.56(1H, d) | | | |
| | | 1715 | 7.18–7.78(4H, m) | | | |
| 125 | 93– | 1320 | 2.12(3H, s) 6.62(1H, d) | 64.77 | 5.78 | 8.90 |
| | 93.5 | 1370 | 3.73(3H, s) 6.77–7.75(6H, m) | (64.94) | (5.77) | (8.91) |
| | | 1415 | 3.92(3H, s) | | | |
| | | 1455 | 5.05(1H, bs) | | | |
| | | 1595 | 5.33(1H, bs) | | | |
| 126 | 110.5– | 1345 1600 | 3.75(3H, s) 7.50–7.82(3H, m) | 60.25 | 4.43 | 14.10 |
| | 111.5 | 1385 2250 | 3.93(3H, s) | (60.18) | (4.37) | (14.03) |
| | | 1415 | 6.68(1H, d) | | | |
| | | 1440 | 6.97(1H, d) | | | |
| | | 1470 | 7.18(2H, d) | | | |
| 127 | oil | 1330 1560 | 1.26(9H, s) 8.46(1H, d) | 56.89 | 5.56 | 12.78 |
| | | 1360* | 3.80(3H, s) | (57.22) | (5.40) | (12.51) |
| | | 1410 | 6.93(1H, d) | | | |
| | | 1460 | 7.39(2H, d) | | | |
| | | 1500 | 7.63(1H, d) | | | |
| 128 | 104– | 1320 3400 | 1.33(9H, s) 8.43(1H, d) | 58.00 | 5.85 | 14.87 |

TABLE 1-continued

| No. of the compound of the present invention | Physical properties and elemental analysis | | | Elemental analysis (%) Found value (Calculated value) | | |
|---|---|---|---|---|---|---|
| | Melting point (°C.) | IR spectrum (cm$^{-1}$, KBr) | NMR spectrum (δ = ppm, CDCl$_3$) | C | H | N |
| | 105 | 1410<br>1455<br>1575<br>1600 | 3.18(3H, d)<br>3.86(3H, s)<br>6.80–7.50(5H, m)<br>8.36(1H, bs) | (57.73) | (5.92) | (14.96) |
| 129 | 133–133.5 | 1335 1600<br>1380 3400<br>1435<br>1495<br>1575 | 1.25(9H, s) 8.34(1H, d)<br>3.09(3H, d)<br>3.77(3H, s)<br>6.73–7.50(5H, m)<br>8.26(1H, bs) | 57.41<br>(57.73) | 5.77<br>(5.92) | 14.62<br>(14.96) |
| 130 | 122.5–123 | 1340 1605<br>1380<br>1430<br>1490<br>1575 | 1.70(4H, mc) 8.23(1H, bs)<br>2.68(4H, mc) 8.32(1H, d)<br>3.08(3H, d)<br>3.76(3H, s)<br>6.59–7.37(4H, m) | 58.28<br>(58.04) | 5.31<br>(5.41) | 14.72<br>(15.04) |
| 131 | oil | 1355*<br>1410<br>1465<br>1550<br>1590 | 1.23(9H, s) 6.70–7.57(5H, m)<br>2.98(6H, s)<br>3.68(3H, s)<br>6.28(1H, d)<br>6.58(1H, d) | 66.46<br>(66.43) | 7.28<br>(7.33) | 12.17<br>(12.23) |
| 132 | 113–114 | 1340 3400<br>1375<br>1410<br>1470<br>1605 | 1.20(9H, s) 6.58(1H, d)<br>2.80(3H, d) 6.92(2H, d)<br>3.61(3H, s) 7.10–7.60(3H, m)<br>4.57(1H, bq)<br>6.18(1H, d) | 65.57<br>(65.62) | 6.88<br>(7.03) | 12.84<br>(12.75) |
| 133 | 73–74 | 1375 3270<br>1420<br>1460<br>1575<br>1605 | 1.22(9H, s) 6.50–7.60(6H, m)<br>2.82(3H, d)<br>3.63(3H, s)<br>4.69(1H, bq)<br>6.20(1H, d) | 65.33<br>(65.62) | 6.96<br>(7.03) | 12.44<br>(12.75) |
| 134 | 78–79 | 1305 1720<br>1340<br>1410<br>1460<br>1580 | 3.50(3H, s) 7.02–7.67(3H, m)<br>3.68(3H, s)<br>3.83(3H, s)<br>6.43(1H, d)<br>6.55–6.83(3H, m) | 62.58<br>(62.49) | 5.48<br>(5.59) | 9.91<br>(9.71) |
| 135 | 64.5–65 | 1320<br>1365<br>1415<br>1460<br>1580 | 3.73(6H s)<br>3.90(3H, s)<br>6.50–7.40(6H, m)<br>7.55(1H, t) | 59.18<br>(59.19) | 5.39<br>(5.29) | 8.99<br>(9.20) |
| 136 | 91.5–92 | 1305 1570<br>1345 1715<br>1405<br>1455<br>1495 | 3.55(3H, s)<br>3.73(3H s)<br>3.88(3H, s)<br>6.46(1H, d)<br>6.65–7.70(6H, m) | 62.37<br>(62.49) | 5.57<br>(5.59) | 9.70<br>(9.71) |
| 137 | 97.5–98.5 | 1325 1600<br>1370<br>1420<br>1460<br>1500 | 3.70(6H, s)<br>3.87(3H, s)<br>6.58(1H, d)<br>6.75–7.12(5H, m)<br>7.53(1H, t) | 59.26<br>(59.19) | 5.47<br>(5.29) | 9.48<br>(9.20) |
| 138 | 68–69 | 1310 1720<br>1345<br>1410<br>1465<br>1585 | 1.36(3H, t) 7.05–7.70(3H, m)<br>3.56(3H, s)<br>3.88(3H, s)<br>3.98(2H, q)<br>6.37–6.90(4H, m) | 63.24<br>(63.56) | 6.11<br>(6.00) | 9.06<br>(9.26) |
| 139 | 66–66.5 | 1320<br>1380<br>1420<br>1465<br>1600 | 1.32(3H, t) 7.55(1H, t)<br>3.70(3H, s)<br>3.88(3H, s)<br>3.95(2H, q)<br>6.50–7.38(6H, m) | 60.40<br>(60.35) | 5.70<br>(5.69) | 8.61<br>(8.79) |
| 140 | 84–85 | 1345 1715<br>1405<br>1460<br>1500<br>1575 | 1.33(3H, t) 6.70–7.67(6H, m)<br>3.54(3H, s)<br>3.87(3H, s)<br>3.93(2H, q)<br>6.43(1H, d) | 63.69<br>(63.56) | 5.95<br>(6.00) | 9.53<br>(9.26) |
| 141 | 96.5–97.5 | 1320 1600<br>1365<br>1415<br>1465<br>1505 | 1.35(3H, t) 7.55(1H, t)<br>3.72(3H, s)<br>3.89(3H, s)<br>3.96(2H, q)<br>6.50–7.12(6H, m) | 60.08<br>(60.35) | 5.53<br>(5.69) | 8.87<br>(8.79) |
| 142 | 53–54 | 1305 1735<br>1345<br>1415<br>1465<br>1585 | 0.75–2.00(7H, m)<br>3.57(3H, s) 6.60–6.90(3H, m)<br>3.90(3H, s) 7.06–7.70(3H, m)<br>3.93(2H, t)<br>6.48(1H, d) | 65.39<br>(65.43) | 6.72<br>(6.71) | 8.36<br>(8.47) |

TABLE 1-continued

| No. of the compound of the present invention | Physical properties and elemental analysis | | | Elemental analysis (%) Found value (Calculated value) | | |
|---|---|---|---|---|---|---|
| | Melting point (°C.) | IR spectrum (cm$^{-1}$, KBr) | NMR spectrum (δ = ppm, CDCl$_3$) | C | H | N |
| 143 | oil | 1320* 1360 1420 1460 1600 | 0.70–2.00(7H, m) 3.73(3H, s) 3.90(2H, t) 3.91(3H, s) 6.45–7.70(7H, m) | 62.64 (62.40) | 6.56 (6.40) | 7.76 (8.08) |
| 144 | 62–62.5 | 1340 1720 1405 1455 1500 1575 | 0.73–2.00(7H, m) 3.53(3H, s) 6.70–7.67(6H, m) 3.87(3H, s) 3.89(2H, t) 6.45(1H, d) | 65.38 (65.43) | 6.81 (6.71) | 8.46 (8.47) |
| 145 | 68–69 | 1320 1600 1360 1415 1465 1505 | 0.75–2.00(7H, m) 3.72(3H, s) 6.77–7.12(5H, m) 3.88(2H, t) 7.57(1H, t) 3.90(3H, s) 6.60(1H, d) | 62.57 (62.40) | 6.30 (6.40) | 8.14 (8.08) |
| 146 | oil | 1320 3380 1360* 1415 1460 1595 | 1.38(3H, d) 6.59(1H, d) 3.03(1H, bs) 6.80–7.15(3H, m) 3.71(3H, s) 7.30(2H, d) 3.88(3H, s) 7.57(1H, t) 4.76(1H, q) | 60.27 (60.35) | 5.56 (5.69) | 9.04 (8.79) |
| 147 | 69.5–71 | 1320 1360 1435 1570 1590 | 1.28(9H, s) 6.73–7.33(5H, m) 1.35(3H, t) 7.54(1H, t) 3.72(3H, s) 4.33(2H, q) 6.57(1H, d) | 66.01 (66.24) | 6.93 (7.02) | 8.32 (8.13) |
| 148 | 106.5–108 | 1320 1360 1410 1460 1595 | 2.43(3H, s) 7.25(2H, d) 3.73(3H, s) 7.58(1H, t) 3.91(3H, s) 6.62(1H, d) 6.85–7.10(3H, m) | 55.98 (56.22) | 4.85 (5.03) | 8.66 (8.74) |
| 149 | 102.5–103.5 | 1330 1375 1420 1480 1600 | 3.73(3H, s) 3.93(3H, s) 5.96(2H, s) 6.40–7.10(5H, m) 7.61(1H, t) | 56.84 (56.59) | 4.54 (4.43) | 8.97 (8.79) |
| 150 | 120–122.5 | 1305 1375 1425 1470 1590 | 2.32(3H, s) 2.73(3H, s) 6.70–7.90(6H, m) 8.50(1H, d) | 57.52 (57.43) | 4.37 (4.47) | 9.79 (9.56) |
| 151 | 82–83.5 | 1305 1380 1470 1580 | 2.33(6H, s) 3.70(3H, s) 6.68–7.70(5H, m) 8.30(1H, bs) | 58.47 (58.72) | 4.81 (4.92) | 8.93 (9.13) |
| 152 | 96–98 | 1285 1375 1415 1470 1575 | 2.28(3H, s) 8.34(1H, d) 2.34(3H, s) 3.55(0.75H, s) 3.63(2.25H, s) 6.60–7.73(5H, m) | 58.77 (58.72) | 4.96 (4.92) | 9.25 (9.13) |
| 153 | 97–98.5 | 1300 1370 1435 1470 1590 | 1.30(3H, t) 7.62(1H, t) 2.33(3H, s) 2.82(2H, q) 3.73(3H, s) 6.70–7.43(5H, m) | 59.91 (59.89) | 5.24 (5.34) | 8.61 (8.73) |
| 154 | 116–118 | 1315 1375 1440 1575 | 2.26(3H, s) 2.32(3H, s) 2.48(3H, s) 3.70(3H, s) 6.66–7.60(5H, m) | 59.74 (59.89) | 5.19 (5.34) | 8.79 (8.73) |
| 155 | 88–89.5 | 1325 1380 1445 1475 1605 | 2.23(6H, s) 2.50(3H, s) 3.68(3H, s) 6.69–7.40(5H m) | 60.03 (59.89) | 5.43 (5.34) | 8.61 (8.73) |
| 156 | 114–115.5 | 1300 1370 1420 1470 1580 | 2.28(3H, s) 3.69(3H, s) 6.65–7.50(5H, m) 7.65(1H, t) | 51.42 (51.38) | 3.61 (3.69) | 8.70 (8.56) |
| 157 | 81–83 | 1295 1360 1415 1460 1595 | 2.32(3H, s) 6.70–7.00(2H, m) 3.06(6H, s) 7.15–7.63(2H, m) 3.71(3H, s) 6.36(1H, d) 6.58(1H, d) | 57.38 (57.22) | 5.41 (5.40) | 12.27 (12.51) |

TABLE 1-continued

| No. of the compound of the present invention | Melting point (°C.) | IR spectrum (cm$^{-1}$, KBr) | NMR spectrum ($\delta$ = ppm, CDCl$_3$) | Elemental analysis (%) Found value (Calculated value) | | |
|---|---|---|---|---|---|---|
| | | | | C | H | N |
| 158 | 73–74.5 | 1310 1365 1395 1460 1580 | 1.35(3H, t) 7.58(1H, t) 2.31(3H, s) 3.91(3H, s) 4.31(2H, q) 6.53–7.43(5H, m) | 57.10 (57.05) | 5.24 (5.08) | 8.37 (8.31) |
| 159 | oil | 1385 1575 1425* 1460 1500 1560 | 1.28(9H, s) 1.32(3H, t) 4.32(2H, q) 6.82–7.78(7H, m) | 62.18 (61.96) | 6.17 (6.06) | 8.03 (8.02) |
| 160 | oil | 1390* 1420 1460 1555 1575 | 1.29(9H, s) 1.33(3H, t) 4.34(2H, q) 6.74–7.81(7H, m) | 61.99 (61.96) | 5.94 (6.06) | 7.80 (8.02) |
| 161 | 57–58 | 1310 1560 1350 1595 1405 1460 1495 | 1.30(9H, s) 6.82–7.14(3H, m) 1.35(3H, t) 7.35(2H, d) 3.91(3H, s) 7.54(1H, t) 4.32(2H, q) 6.61(1H, d) | 65.85 (66.24) | 6.92 (7.02) | 8.46 (8.13) |
| 162 | 75.5–76.5 | 1320 1595 1400 1425 1455 1570 | 1.30(9H, s) 6.73–7.35(5H, m) 1.37(3H, t) 7.57(1H, t) 3.93(3H, s) 4.35(2H, q) 6.62(1H, d) | 65.95 (66.24) | 7.21 (7.02) | 8.38 (8.13) |
| 163 | oil | 1320 1490 1350 1600 1400* 1425 1465 | 1.28(3H, t) 6.43–7.15(5H, m) 1.64(4H, mc) 7.47(1H, t) 2.63(4H, mc) 3.82(3H, s) 4.23(2H, q) | 66.82 (66.63) | 6.60 (6.47) | 7.81 (8.18) |
| 164 | oil | 1360 1575 1390* 1420 1455 1560 | 0.95(3H, t) 1.32(9H, s) 1.80(2H, sex) 4.26(2H, t) 6.75–7.82(7H, m) | 63.24 (62.88) | 6.53 (6.38) | 7.39 (7.71) |
| 165 | 62–64 | 1315 1595 1420 1455 1500 1565 | 0.88(3H, t) 6.56(1H, d) 1.23(9H, s) 6.80–7.07(3H, m) 1.76(2H, sex) 7.30(2H, d) 3.85(3H, s) 7.51(1H, t) 4.19(2H, t) | 66.73 (67.00) | 7.40 (7.31) | 8.05 (7.81) |
| 166 | oil | 1320 1570 1360 1600 1400* 1425 1460 | 0.95(3H, t) 6.59(1H, d) 1.30(9H, s) 6.75–7.35(5H, m) 1.83(2H, sex) 7.52(1H, t) 3.89(3H, s) 4.25(2H, t) | 66.83 (67.00) | 7.37 (7.31) | 7.60 (7.81) |
| 167 | oil | 1320 1570 1400 1600 1425* 1460 1490 | 0.97(3H, t) 6.50–7.18(5H, m) 1.77(6H, mc) 7.53(1H, t) 2.72(4H, mc) 3.90(3H, s) 4.25(2H, t) | 67.28 (67.38) | 6.81 (6.78) | 7.50 (7.85) |
| 168 | oil | 1305 1560 1345 1595 1405* 1460 1500 | 1.32(6H, d) 6.82–7.83(6H, m) 1.33(9H, s) 3.94(3H, s) 5.39(1H, h) 6.71(1H, d) | 66.90 (67.00) | 7.34 (7.31) | 7.63 (7.81) |
| 169 | oil | 1315* 1350 1410 1465 1600 | 1.26(6H d) 1.28(9H, s) 3.91(3H, s) 5.37(1H, h) 6.53–7.79(7H, m) | 66.91 (67.00) | 7.49 (7.31) | 8.09 (7.81) |
| 170 | oil | 1310 1600 1350* 1405 1465 1490 | 1.25(6H, d) 6.53–7.21(5H, m) 1.70(4H, mc) 7.55(1H, t) 2.68(4H, mc) 3.87(3H, s) 5.32(1H, h) | 67.48 (67.38) | 6.73 (6.78) | 7.89 (7.85) |
| 171 | 53–55 | 1305 1710 1340 1410 1460 1580 | 0.75(3H, t) 6.32(1H, d) 1.46(2H, sex) 6.75–7.55(6H, m) 2.41(2H, t) 3.40(3H, s) 3.73(3H, s) | 67.81 (67.98) | 6.68 (6.71) | 9.19 (9.32) |
| 172 | 40–42 | 1320 1600 1360 1420 1460 | 0.90(3H, t) 6.58(1H, d) 1.60(2H, sex) 6.78–7.33(5H, m) 2.56(2H, t) 7.53(1H, t) 3.72(3H, s) | 64.49 (64.53) | 6.31 (6.37) | 8.97 (8.85) |

TABLE 1-continued

| No. of the compound of the present invention | Melting point (°C.) | IR spectrum (cm$^{-1}$, KBr) | NMR spectrum (δ = ppm, CDCl$_3$) | Elemental analysis (%) Found value (Calculated value) | | |
|---|---|---|---|---|---|---|
| | | | | C | H | N |
| 173 | 85.5–87 | 1300 1575<br>1340 1720<br>1405<br>1455<br>1505<br>1570 | 3.89(3H, s)<br>2.60(3H, s) 7.58(1H, t)<br>3.58(3H, s) 8.01(1H, d)<br>3.92(3H, s)<br>6.53(1H, d)<br>6.93–7.37(3H, m) | 56.70<br>(56.78) | 4.75<br>(4.76) | 13.32<br>(13.24) |
| 174 | 59–61 | 1320 1515<br>1340 1580<br>1370<br>1420<br>1460 | 2.59(3H, s) 7.63(1H, t)<br>3.74(3H, s) 8.06(1H, d)<br>3.92(3H, s)<br>6.68(1H, d)<br>6.88–7.30(3H, m) | 53.90<br>(54.04) | 4.45<br>(4.53) | 12.78<br>(12.60) |
| 175 | 78–79 | 1325<br>1360<br>1420<br>1465<br>1620 | 2.31(3H, s) 6.77–7.25(4H, m)<br>2.42(3H, s) 7.56(1H, t)<br>3.73(3H, s)<br>3.91(3H, s)<br>6.58(1H, d) | 57.59<br>(57.45) | 5.53<br>(5.42) | 8.60<br>(8.37) |
| 176 | 76–77.5 | 1320<br>1375<br>1425<br>1465<br>1585 | 3.77(3H, s)<br>6.93–8.00(7H, m)<br>8.53(1H, d) | 53.63<br>(53.84) | 3.67<br>(3.55) | 9.04<br>(8.96) |
| 177 | 121–122.5 | 1330 1595<br>1380<br>1445<br>1470<br>1480 | 2.56(3H, s)<br>3.73(3H, s)<br>6.93–7.83(7H, m) | 55.42<br>(55.20) | 4.11<br>(4.01) | 8.38<br>(8.58) |
| 178 | 95.5–97 | 1320<br>1390<br>1480<br>1595 | 2.53(3H, s)<br>3.73(3H, s)<br>7.00–7.83(6H, m)<br>8.40(1H, bs) | 55.06<br>(55.20) | 4.19<br>(4.01) | 8.97<br>(8.58) |
| 179 | 94–96 | 1330<br>1385<br>1415<br>1480<br>1605 | 2.38(3H, s)<br>3.72(3H, s)<br>6.95–7.77(6H, m)<br>8.37(1H, d) | 54.92<br>(55.20) | 4.11<br>(4.01) | 8.41<br>(8.58) |
| 180 | oil | 1325*<br>1385<br>1420<br>1485<br>1610 | 2.37(3H, s)<br>3.60(0.5H, s)<br>3.66(2.5H, s)<br>6.96–7.83(6H, m)<br>8.40(1H, d) | 55.15<br>(55.20) | 3.90<br>(4.01) | 8.26<br>(8.58) |
| 181 | 100.5–103 | 1330<br>1380<br>1480<br>1580 | 2.27(3H, s)<br>2.49(3H, s)<br>3.72(3H, s)<br>7.00–7.80(6H, m) | 56.16<br>(56.46) | 4.48<br>(4.44) | 8.44<br>(8.23) |
| 182 | 100–102.5 | 1320<br>1385<br>1410<br>1485<br>1605 | 2.33(3H, s) 7.15(2H, d)<br>2.50(3H, s) 7.58(2H, d)<br>3.72(3H, s)<br>6.90(1H, s)<br>7.00(1H, s) | 56.57<br>(56.46) | 4.44<br>(4.44) | 8.15<br>(8.23) |
| 183 | 78.5–80 | 1320<br>1375<br>1440<br>1480<br>1595 | 1.30(3H, t)<br>2.83(2H, q)<br>3.75(3H, s)<br>6.93–7.87(7H, m) | 56.59<br>(56.46) | 4.63<br>(4.44) | 8.11<br>(8.23) |
| 184 | 128.5–130 | 1325<br>1375<br>1430<br>1480<br>1580 | 3.78(3H, s)<br>7.03–7.95(7H, m) | 48.39<br>(48.49) | 3.07<br>(2.90) | 7.88<br>(8.07) |
| 185 | 133–135 | 1330<br>1380<br>1435<br>1485<br>1580 | 3.77(3H, s)<br>7.03–7.83(7H, m) | 42.96<br>(42.98) | 2.52<br>(2.57) | 7.34<br>(7.16) |
| 186 | 74–76 | 1335<br>1375<br>1430<br>1485<br>1605 | 3.07(6H, s)<br>3.72(3H, s)<br>6.38(1H, d)<br>6.58(1H, d)<br>7.00–7.78(7H, m) | 53.80<br>(54.07) | 4.46<br>(4.53) | 11.66<br>(11.82) |
| 187 | 132–134 | 1305<br>1375<br>1420<br>1470<br>1580 | 2.32(3H, s)<br>3.71(3H, s)<br>6.67–7.70(6H, m) | 45.19<br>(45.24) | 3.31<br>(3.25) | 7.33<br>(7.53) |

TABLE 1-continued

| No. of the compound of the present invention | Melting point (°C.) | IR spectrum (cm⁻¹, KBr) | NMR spectrum (δ = ppm, CDCl₃) | Elemental analysis (%) Found value (Calculated value) | | |
|---|---|---|---|---|---|---|
| | | | | C | H | N |
| 188 | 111–113 | 1325<br>1360<br>1425<br>1450<br>1600 | 2.90(6H, s)<br>3.73(3H, s)<br>3.90(3H, s)<br>6.30–7.36(6H, m)<br>7.58(1H, t) | 60.78<br>(60.54) | 6.05<br>(6.03) | 13.37<br>(13.23) |
| 189 | 75–76 | 1350 1720<br>1415<br>1465<br>1505<br>1590 | 2.90(6H, s)<br>3.57(3H, s)<br>3.89(3H, s)<br>6.37–6.67(4H, m)<br>7.00–7.70(3H, m) | 63.71<br>(63.77) | 6.24<br>(6.35) | 13.71<br>(13.94) |
| 190 | 52–54 | 1350<br>1415<br>1465<br>1585<br>1720 | 3.57(3H, s)<br>3.90(3H, s)<br>6.51(1H, d)<br>6.97–8.03(6H, m)<br>9.93(1H, s) | 62.86<br>(62.93) | 4.83<br>(4.92) | 9.80<br>(9.78) |
| 191 | oil | 1330*<br>1370<br>1425<br>1470<br>1605 | 2.00(3H, d) 6.85–7.75(6H, m)<br>3.73(3H, s)<br>3.90(3H, s)<br>5.20(1H, q)<br>6.63(1H, d) | 50.35<br>(50.40) | 4.36<br>(4.49) | 7.50<br>(7.34) |
| 192 | 43–45 | 1325<br>1400<br>1435<br>1590 | 1.39(3H, t) 7.18(2H, d)<br>3.95(3H, s) 7.62(2H, d)<br>4.33(2H, q) 7.63(1H, t)<br>6.70(1H, d)<br>6.94(1H, d) | 54.06<br>(53.92) | 4.13<br>(4.24) | 7.87<br>(7.86) |
| 193 | oil | 1315 1500<br>1350 1600<br>1400*<br>1425<br>1460 | 1.20(3H, t) 6.62(1H, d)<br>1.35(3H, t) 6.82–7.40(5H, m)<br>2.64(2H, q) 7.56(1H, t)<br>3.92(3H, s)<br>4.33(2H, q) | 64.50<br>(64.53) | 6.46<br>(6.37) | 8.49<br>(8.85) |
| 194 | 53–54 | 1310 1595<br>1395<br>1425<br>1450<br>1495 | 1.23(6H, d) 6.59(1H, d)<br>1.33(3H, t) 6.77–7.35(5H, m)<br>2.87(1H, h) 7.53(1H, t)<br>3.92(3H, s)<br>4.30(2H, q) | 65.17<br>(65.42) | 6.67<br>(6.71) | 8.63<br>(8.47) |
| 195 | oil | 1325*<br>1410<br>1435<br>1470<br>1610 | 1.35(3H, t) 6.47–7.38(5H, m)<br>2.05(2H, p) 7.55(1H, t)<br>2.87(4H, t)<br>3.90(3H, s)<br>4.32(2H, q) | 65.54<br>(65.82) | 6.13<br>(6.13) | 8.18<br>(8.52) |
| 196 | oil | 1320 1600<br>1350*<br>1400<br>1425<br>1465 | 0.86–2.08(9H, m) 7.53(1H, t)<br>3.28(2H, bs)<br>3.88(3H, s)<br>4.28(2H, q)<br>6.41–7.26(5H, m) | 67.77<br>(67.76) | 6.35<br>(6.25) | 8.23<br>(7.90) |
| 197 | 80–82 | 1305 1585<br>1410<br>1430<br>1465<br>1495 | 1.37(3H, t) 8.53(1H, d)<br>1.77(4H, mc)<br>2.75(4H, mc)<br>4.36(2H, q)<br>6.55–7.96(6H, m) | 69.56<br>(69.19) | 6.27<br>(6.45) | 8.70<br>(8.96) |
| 198 | 76.5–78.5 | 1305 1595<br>1350<br>1370<br>1415<br>1455 | 1.28(3H, t) 6.57–7.78(6H, m)<br>1.72(4H, mc)<br>2.55(3H, s)<br>2.72(4H, mc)<br>4.31(2H, q) | 70.25<br>(69.90) | 6.84<br>(6.79) | 8.72<br>(8.58) |
| 199 | 70.5–72.5 | 1300 1570<br>1350<br>1385<br>1425<br>1495 | 1.32(3H, t)<br>1.75(4H, mc)<br>2.73(4H, mc)<br>4.30(2H, q)<br>6.60–7.77(6H, m) | 55.37<br>(55.24) | 4.73<br>(4.89) | 7.21<br>(7.15) |
| 200 | oil | 1330 1730<br>1385*<br>1440<br>1475<br>1585 | 1.42(3H, t) 6.53(1H, d)<br>1.82(4H, mc) 6.72–7.72(5H, m)<br>2.80(4H, mc)<br>3.95(3H, s)<br>4.20(2H, q) | 69.66<br>(69.91) | 6.70<br>(6.79) | 8.32<br>(8.58) |
| 201 | oil | 1330*<br>1375<br>1425<br>1470<br>1605 | 3.36(3H, s) 6.90–7.20(3H, m)<br>3.75(3H, s) 7.35(2H, d)<br>3.93(3H, s) 7.62(1H, t)<br>4.45(2H, s)<br>6.65(1H, d) | 60.18<br>(60.35) | 5.73<br>(5.69) | 9.08<br>(8.79) |
| 202 | oil | 1325 1600<br>1365*<br>1420<br>1460 | 0.71–1.90(7H, m)<br>2.62(2H, t) 6.78–7.31(5H, m)<br>3.75(3H, s) 7.65(1H, t)<br>3.91(3H, s) | 65.62<br>(65.42) | 6.59<br>(6.71) | 8.78<br>(8.47) |

TABLE 1-continued

| No. of the compound of the present invention | Physical properties and elemental analysis | | | | | |
|---|---|---|---|---|---|---|
| | Melting point (°C.) | IR spectrum (cm$^{-1}$, KBr) | NMR spectrum (δ = ppm, CDCl$_3$) | Elemental analysis (%) Found value (Calculated value) | | |
| | | | | C | H | N |
| 203 | 106–108 | 1500 1320 1580 1360 1415 1455 1565 | 6.60(1H, d) 3.81(3H, s) 3.93(3H, s) 6.67(1H, d) 7.08–8.33(8H, m) | 62.53 (62.75) | 4.79 (4.64) | 12.63 (12.91) |

*NaCl

In order to use compounds of the present invention as herbicides, proper amount of one or more than one of the compounds represented by the above-stated general formula (I) is incorporated with inert carriers to use as usual agricultural chemicals like water dispersible powder, emulsifiable concentrate, granules, dust and so on.

As solid carriers, talc, clay, diatomaceous earth, bentonite, kaolin, Japanese acid clay, white carbon, pumice powder and the like are exemplified. As liquid carriers, water, alcohol, benzene, toluene, xylene, kerosine, cyclohexane, cyclohexanone, isophorone, Butyl Cellosolve, benzyl acetate, dimethylformamide, mineral oil and the like are used.

Furthermore, surface-active agents and stabilizers can be added when they are required. In addition, the herbicides of the present invention can be applied after incorporating them with other agricultural chemicals used in the same field, for example, insecticides, fungicides, herbicides, plant growth regulators or fertilizers. Especially, there will be occasions for the herbicides containing the compounds of the present invention that it is proper to be mixed with other herbicides for the purpose of reducing labor for spreading or for the purpose of extending the spectrum of weed species to be effectively prevented.

As herbicides to be added, triazine herbicides such as Atrazine, Simazine, Simetryn, Prometryn and the like; carbamate herbicides such as Asulam, Benthiocarb, Molinate and the like; urea herbicides such as Linuron, Dymrone and the like; phenoxy-series herbicides such as 2,4-D, MCP, MCPB, Naproanilide and the like; diphenyl ether herbicides such as Nitrofen, Chlornitrofen, Chlomethoxynil and the like; heterocyclic-series herbicides such as Oxadiazon, Pyrazolate, Bentazon and the like; and amide herbicides such as Alachlor, Butachlor, Propanil and the like can be exemplified. It is possible to provide mixtures of the compounds of the present invention by being skillfully combined with one or more than one of the herbicides described above to be effective to many weed species.

Examples of the formulation in which the compounds of the present invention were used are explained hereinbelow. In the Examples, the term "parts" means parts by weight.

EXAMPLE 5

Water dispersible powder

A mixture of the compound No. 14 of the present invention (10 parts), Zeeklite (Trade Name, manufactured by Kunimine Kogyo Co., Ltd., 87.3 parts) used as the carrier material, Neopelex (Trade Name, manufactured by Kao Atlas Co., Ltd., 1.35 parts), and Solpol 800A (Trade Name, manufactured by Toho Kogyo Co., Ltd., 1.35 parts) was pulverized to give 10% water dispersible powder.

EXAMPLE 6

Emulsifiable concentrate

A mixture of the compound No. 15 of the present invention (25 parts) and Solpol 800A (10 parts) was dissolved in 65 parts of benzene to give 25% emulsifiable concentrate.

EXAMPLE 7

Granules

A mixture of the compound No. 24 of the present invention (10 parts), 50 parts of bentonite, 35 parts of Kunilite (Trade Name, manufactured by Kokuho Kogyo Co., Ltd.) and 5 parts of Solpol 800A used as the surface-active agent was pulverized. After 10 parts of water was added, the mixture was kneaded to give a homogeneous mixture and then the mixture was extruded through sieving perforations having a diameter of 0.7 mm and dried. The product was cut off to give 10% granules having length of 1–2 mm.

The compounds of the present invention are suitable for an active ingredient of herbicides since the herbicides containing these compounds do not show any phytotoxity against many useful crops like rice, soybean, cotton and the like but have excellent herbicidal activity against various weeds. More particularly, as to the herbicidal action of the compounds of the present invention, characteristic features are that the compounds kill weeds, or inhibit the growth, or suppress the growth considerably to result in a failure of growth competition against crops.

Application amount of the compounds of the present invention is generally in the range of 10 to 1000 g/10 ares, preferably 50 to 500 g/10 ares as an active ingredient although it differs depending upon the place applied, the application time, the application methods, and weeds to be avoided.

The compounds of the present invention were found to have outstanding herbicidal activity against barnyard grass as well as many weeds such as umbrella plant, monochoria, tooth cup, bulrush and so on in the use of 50–500 g/10 ares as an active ingredient, especially under submerged paddy field condition. In addition, the compounds of the present invention are highly safe to young seedling of rice plants and no affection has been observed even in the application amount of 1000 g/10 ares as an active ingredient. Therefore, the compounds of the present invention have extremely excellent characteristics as an active ingredient of herbicides to be used for paddy field. Furthermore, the application period can be considerably extended since some of the compounds of the present invention have good herbicidal activity against barnyard grass even in a growth period (1- to 3-leaf stage). That is to say, it was shown that these compounds have high applicability as an active ingredient of soil-applied herbicides in a cultivation of transplanted rice plants at the primary to medium stage and immediately after flooding in a cultivation of dry-seeded rice.

Surprisingly, it was also shown that the herbicides containing some of the compounds of the present invention have high applicability to be used in farmland because those herbicides, when they are used as soil-applied agents after the seeding of general broadleaved crops like soybean, effectively prevent gramineous weeds such as barnyard grass, crab grass, and foxtail without any phytotoxity to crops.

The herbicidal effects of the compounds of the present invention are explained in the below-stated Examples.

EXAMPLE 8

Test for the herbicidal effects under submerged conditions (I)

Paddy field soil was charged in porcelain pots having a diameter of 9 cm, and then water was added. After the soil was tilled, weed seeds were sown on the surface of the soil and two bunches of rice plants (variety: Nihonbare) being in 2-leaf stage were transplanted in 1 cm depth. The pots were flooded to give water depth of 2 cm on the next day and predetermined amount of water dispersible powder of the compounds of the present invention, which was dispersed in 10 ml of water, was added dropwise into every pots on the surface of water for the treatment. Then they were settled in a greenhouse and received water in proper time intervals. After 3 weeks from the treatment with chemicals, the herbicidal effects as well as the influences against the rice plants were examined. Evaluation is expressed by 6 stage system, details of which are shown below. The obtained results are shown in Table 2.

| Expression | Phytotoxicity against rice plants | Herbicidal effects |
|---|---|---|
| 5 | Killed | 100% Prevention (Amount of residual weeds: 0%) |
| 5 | Considerably injured | 80% Prevention (Amount of residual weeds: 20%) |
| 3 | Substantially injured | 60% Prevention (Amount of residual weeds: 40%) |
| 2 | A little injured | 40% Prevention (Amount of residual weeds: 60%) |
| 1 | Slightly injured | 20% Prevention (Amount of residual weeds: 80%) |
| 0 | No injured | 0% Prevention (Amount of residual weeds: 100%) |

TABLE 2

| The compounds of the present invention | | Phytotoxicity against rice plant | Herbicidal effect | | | | |
|---|---|---|---|---|---|---|---|
| No. | Dose (g/10 ares) | | Barnyard grass | Umbrella plant | Bulrush | Monochoria | Tooth cup |
| 13 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 14 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 15 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 17 | 125 | 0 | 5 | 5 | 4 | 5 | 4 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 18 | 125 | 0 | 5 | 5 | 5 | 5 | 4 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 19 | 125 | 0 | 5 | 5 | 0 | 3 | 2 |
|  | 250 | 0 | 5 | 5 | 1 | 4 | 3 |
|  | 500 | 0 | 5 | 5 | 1 | 4 | 3 |
|  | 1000 | 0 | 5 | 5 | 2 | 4 | 4 |
| 20 | 125 | 0 | 5 | 5 | 1 | 4 | 4 |
|  | 250 | 0 | 5 | 5 | 1 | 5 | 5 |
|  | 500 | 0 | 5 | 5 | 2 | 5 | 5 |
|  | 1000 | 0 | 5 | 5 | 3 | 5 | 5 |
| 23 | 125 | 0 | 5 | 5 | 1 | 5 | 5 |
|  | 250 | 0 | 5 | 5 | 1 | 5 | 5 |
|  | 500 | 0 | 5 | 5 | 2 | 5 | 5 |
|  | 1000 | 0 | 5 | 5 | 3 | 5 | 5 |
| 24 | 125 | 0 | 5 | 5 | 1 | 5 | 5 |
|  | 250 | 0 | 5 | 5 | 3 | 5 | 5 |
|  | 500 | 0 | 5 | 5 | 4 | 5 | 5 |
|  | 1000 | 0 | 5 | 5 | 5 | 5 | 5 |
| 27 | 125 | 0 | 5 | 5 | 3 | 4 | 4 |
|  | 250 | 0 | 5 | 5 | 3 | 5 | 5 |
|  | 500 | 0 | 5 | 5 | 5 | 5 | 5 |
|  | 1000 | 0 | 5 | 5 | 5 | 5 | 5 |
| 28 | 125 | 0 | 5 | 5 | 5 | 5 | 5 |
|  | 250 | 0 | 5 | 5 | 5 | 5 | 5 |

TABLE 2-continued

| The compounds of the present invention | | Phytotoxicity against rice plant | Herbicidal effect | | | | |
|---|---|---|---|---|---|---|---|
| No. | Dose (g/10 ares) | | Barnyard grass | Umbrella plant | Bulrush | Monochoria | Tooth cup |
| | 500 | 0 | 5 | 5 | 5 | 5 | 5 |
| | 1000 | 0 | 5 | 5 | 5 | 5 | 5 |
| 29 | 125 | 0 | 5 | 5 | 4 | 5 | 5 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 30 | 125 | 0 | 5 | 5 | 4 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 32 | 125 | 0 | 5 | 5 | 2 | 3 | 4 |
| | 250 | 0 | 5 | 5 | 2 | 4 | 5 |
| | 500 | 0 | 5 | 5 | 3 | 5 | 5 |
| | 1000 | 0 | 5 | 5 | 4 | 5 | 5 |
| 34 | 125 | 0 | 5 | 5 | 3 | 5 | 5 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 36 | 125 | 0 | 5 | 5 | 2 | 5 | 5 |
| | 250 | 0 | 5 | 5 | 3 | 5 | 5 |
| | 500 | 0 | 5 | 5 | 3 | 5 | 5 |
| | 1000 | 0 | 5 | 5 | 5 | 5 | 5 |
| 37 | 125 | 0 | 5 | 5 | 1 | 5 | 5 |
| | 250 | 0 | 5 | 5 | 2 | 5 | 5 |
| | 500 | 0 | 5 | 5 | 2 | 5 | 5 |
| | 1000 | 0 | 5 | 5 | 3 | 5 | 5 |
| 38 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 39 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 45 | 125 | 0 | 5 | 5 | 1 | 5 | 4 |
| | 250 | 0 | 5 | 5 | 2 | 5 | 5 |
| | 500 | 0 | 5 | 5 | 3 | 5 | 5 |
| | 1000 | 0 | 5 | 5 | 3 | 5 | 5 |
| 47 | 125 | 0 | 5 | 5 | 2 | 4 | 2 |
| | 250 | 0 | 5 | 5 | 3 | 5 | 3 |
| | 500 | 0 | 5 | 5 | 3 | 5 | 4 |
| | 1000 | 0 | 5 | 5 | 4 | 5 | 4 |
| 49 | 125 | 0 | 5 | 5 | 2 | 5 | 5 |
| | 250 | 0 | 5 | 5 | 3 | 5 | 5 |
| | 500 | 0 | 5 | 5 | 3 | 5 | 5 |
| | 1000 | 0 | 5 | 5 | 3 | 5 | 5 |
| 50 | 125 | 0 | 5 | 5 | 4 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 51 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 52 | 125 | 0 | 5 | 5 | 1 | 5 | 5 |
| | 250 | 0 | 5 | 5 | 1 | 5 | 5 |
| | 500 | 0 | 5 | 5 | 2 | 5 | 5 |
| | 1000 | 0 | 5 | 5 | 2 | 5 | 5 |
| 53 | 125 | 0 | 5 | 5 | 2 | 5 | 5 |
| | 250 | 0 | 5 | 5 | 2 | 5 | 5 |
| | 500 | 0 | 5 | 5 | 2 | 5 | 5 |
| | 1000 | 0 | 5 | 5 | 3 | 5 | 5 |
| 54 | 125 | 0 | 5 | 5 | 1 | 5 | 5 |
| | 250 | 0 | 5 | 5 | 1 | 5 | 5 |
| | 500 | 0 | 5 | 5 | 2 | 5 | 5 |
| | 1000 | 0 | 5 | 5 | 3 | 5 | 5 |
| 58 | 125 | 0 | 5 | 5 | 4 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 62 | 125 | 0 | 5 | 5 | 2 | 5 | 4 |
| | 250 | 0 | 5 | 5 | 3 | 5 | 5 |
| | 500 | 0 | 5 | 5 | 4 | 5 | 5 |
| | 1000 | 0 | 5 | 5 | 4 | 5 | 5 |
| 63 | 125 | 0 | 5 | 5 | 2 | 5 | 4 |
| | 250 | 0 | 5 | 5 | 3 | 5 | 5 |
| | 500 | 0 | 5 | 5 | 4 | 5 | 5 |
| | 1000 | 0 | 5 | 5 | 4 | 5 | 5 |

TABLE 2-continued

| The compounds of the present invention | | Phytotoxicity against rice plant | Herbicidal effect | | | | |
|---|---|---|---|---|---|---|---|
| No. | Dose (g/10 ares) | | Barnyard grass | Umbrella plant | Bulrush | Monochoria | Tooth cup |
| 64 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 67 | 125 | 0 | 5 | 5 | 0 | 5 | 5 |
|  | 250 | 0 | 5 | 5 | 0 | 5 | 5 |
|  | 500 | 0 | 5 | 5 | 1 | 5 | 5 |
|  | 1000 | 0 | 5 | 5 | 1 | 5 | 5 |
| 72 | 125 | 0 | 5 | 5 | 1 | 5 | 5 |
|  | 250 | 0 | 5 | 5 | 2 | 5 | 5 |
|  | 500 | 0 | 5 | 5 | 3 | 5 | 5 |
|  | 1000 | 0 | 5 | 5 | 3 | 5 | 5 |
| 78 | 125 | 0 | 5 | 5 | 4 | 5 | 5 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 79 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 83 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 85 | 125 | 0 | 5 | 5 | 0 | 5 | 5 |
|  | 250 | 0 | 5 | 5 | 1 | 5 | 5 |
|  | 500 | 0 | 5 | 5 | 2 | 5 | 5 |
|  | 1000 | 0 | 5 | 5 | 2 | 5 | 5 |
| 87 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 89 | 125 | 0 | 5 | 5 | 2 | 5 | 5 |
|  | 250 | 0 | 5 | 5 | 3 | 5 | 5 |
|  | 500 | 0 | 5 | 5 | 4 | 5 | 5 |
|  | 1000 | 0 | 5 | 5 | 4 | 5 | 5 |
| 90 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 92 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 94 | 125 | 0 | 5 | 5 | 0 | 3 | 5 |
|  | 250 | 0 | 5 | 5 | 1 | 4 | 5 |
|  | 500 | 0 | 5 | 5 | 2 | 4 | 5 |
|  | 1000 | 0 | 5 | 5 | 2 | 5 | 5 |
| 96 | 125 | 0 | 5 | 5 | 5 | 4 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 98 | 125 | 0 | 4 | 5 | 4 | 3 | 5 |
|  | 250 | 0 | 5 | 5 | 4 | 4 | 5 |
|  | 500 | 0 | 5 | 5 | 5 | 5 | 5 |
|  | 1000 | 0 | 5 | 5 | 5 | 5 | 5 |
| 99 | 125 | 0 | 5 | 5 | 4 | 5 | 4 |
|  | 250 | 0 | 5 | 5 | 4 | 5 | 4 |
|  | 500 | 0 | 5 | 5 | 5 | 5 | 5 |
|  | 1000 | 0 | 5 | 5 | 5 | 5 | 5 |
| 101 | 125 | 0 | 5 | 5 | 4 | 4 | 4 |
|  | 250 | 0 | 5 | 5 | 4 | 4 | 5 |
|  | 500 | 0 | 5 | 5 | 5 | 5 | 5 |
|  | 1000 | 0 | 5 | 5 | 5 | 5 | 5 |
| 102 | 125 | 0 | 5 | 5 | 4 | 4 | 2 |
|  | 250 | 0 | 5 | 5 | 4 | 4 | 3 |
|  | 500 | 0 | 5 | 5 | 5 | 5 | 3 |
|  | 1000 | 0 | 5 | 5 | 5 | 5 | 4 |
| 104 | 125 | 0 | 5 | 5 | 2 | 4 | 4 |
|  | 250 | 0 | 5 | 5 | 3 | 5 | 5 |
|  | 500 | 0 | 5 | 5 | 4 | 5 | 5 |
|  | 1000 | 0 | 5 | 5 | 4 | 5 | 5 |
| 105 | 125 | 0 | 0 | 3 | 2 | 3 | 2 |
|  | 250 | 0 | 1 | 4 | 3 | 4 | 3 |
|  | 500 | 0 | 2 | 5 | 4 | 4 | 4 |
|  | 1000 | 0 | 2 | 5 | 4 | 5 | 4 |
| 106 | 125 | 0 | 5 | 5 | 4 | 5 | 2 |
|  | 250 | 0 | 5 | 5 | 4 | 5 | 2 |

TABLE 2-continued

| The compounds of the present invention | | Phytotoxicity against rice plant | Herbicidal effect | | | | |
|---|---|---|---|---|---|---|---|
| No. | Dose (g/10 ares) | | Barnyard grass | Umbrella plant | Bulrush | Monochoria | Tooth cup |
| | 500 | 0 | 5 | 5 | 5 | 5 | 3 |
| | 1000 | 0 | 5 | 5 | 5 | 5 | 3 |
| 108 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 113 | 125 | 0 | 5 | 5 | 5 | 5 | 4 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 117 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 119 | 125 | 0 | 5 | 5 | 5 | 4 | 2 |
| | 250 | 0 | 5 | 5 | 5 | 5 | 3 |
| | 500 | 0 | 5 | 5 | 5 | 5 | 4 |
| | 1000 | 0 | 5 | 5 | 5 | 5 | 4 |
| 120 | 125 | 0 | 2 | 5 | 3 | 5 | 3 |
| | 250 | 0 | 3 | 5 | 4 | 5 | 4 |
| | 500 | 0 | 4 | 5 | 5 | 5 | 5 |
| | 1000 | 0 | 4 | 5 | 5 | 5 | 5 |
| 122 | 125 | 0 | 2 | 5 | 2 | 4 | 5 |
| | 250 | 0 | 2 | 5 | 3 | 5 | 5 |
| | 500 | 0 | 3 | 5 | 4 | 5 | 5 |
| | 1000 | 0 | 5 | 5 | 4 | 5 | 5 |
| 125 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 126 | 125 | 0 | 1 | 4 | 1 | 2 | 0 |
| | 250 | 0 | 1 | 5 | 1 | 2 | 1 |
| | 500 | 0 | 2 | 5 | 2 | 3 | 1 |
| | 1000 | 0 | 2 | 5 | 2 | 3 | 2 |
| 127 | 125 | 0 | 5 | 5 | 2 | 5 | 3 |
| | 250 | 0 | 5 | 5 | 2 | 5 | 4 |
| | 500 | 0 | 5 | 5 | 3 | 5 | 4 |
| | 1000 | 0 | 5 | 5 | 4 | 5 | 5 |
| 130 | 125 | 0 | 3 | 5 | 2 | 5 | 5 |
| | 250 | 0 | 3 | 5 | 4 | 5 | 5 |
| | 500 | 0 | 5 | 5 | 5 | 5 | 5 |
| | 1000 | 0 | 5 | 5 | 5 | 5 | 5 |
| 132 | 125 | 0 | 5 | 5 | 3 | 5 | 4 |
| | 250 | 0 | 5 | 5 | 4 | 5 | 5 |
| | 500 | 0 | 5 | 5 | 4 | 5 | 5 |
| | 1000 | 0 | 5 | 5 | 5 | 5 | 5 |
| 137 | 125 | 0 | 5 | 5 | 4 | 5 | 3 |
| | 250 | 0 | 5 | 5 | 5 | 5 | 4 |
| | 500 | 0 | 5 | 5 | 5 | 5 | 4 |
| | 1000 | 0 | 5 | 5 | 5 | 5 | 5 |
| 142 | 125 | 0 | 5 | 5 | 4 | 5 | 3 |
| | 250 | 0 | 5 | 5 | 5 | 5 | 4 |
| | 500 | 0 | 5 | 5 | 5 | 5 | 5 |
| | 1000 | 0 | 5 | 5 | 5 | 5 | 5 |
| 146 | 125 | 0 | 2 | 5 | 2 | 2 | 2 |
| | 250 | 0 | 4 | 5 | 2 | 3 | 3 |
| | 500 | 0 | 4 | 5 | 3 | 4 | 4 |
| | 1000 | 0 | 5 | 5 | 4 | 5 | 5 |
| 149 | 125 | 0 | 5 | 5 | 4 | 4 | 3 |
| | 250 | 0 | 5 | 5 | 5 | 5 | 3 |
| | 500 | 0 | 5 | 5 | 5 | 5 | 4 |
| | 1000 | 0 | 5 | 5 | 5 | 5 | 4 |
| 153 | 125 | 0 | 5 | 5 | 3 | 5 | 3 |
| | 250 | 0 | 5 | 5 | 3 | 5 | 3 |
| | 500 | 0 | 5 | 5 | 4 | 5 | 4 |
| | 1000 | 0 | 5 | 5 | 4 | 5 | 4 |
| 155 | 125 | 0 | 4 | 5 | 4 | 4 | 3 |
| | 250 | 0 | 5 | 5 | 5 | 5 | 3 |
| | 500 | 0 | 5 | 5 | 5 | 5 | 4 |
| | 1000 | 0 | 5 | 5 | 5 | 5 | 4 |
| 157 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 163 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |

TABLE 2-continued

| The compounds of the present invention | | Phytotoxicity against rice plant | Herbicidal effect | | | | |
|---|---|---|---|---|---|---|---|
| No. | Dose (g/10 ares) | | Barnyard grass | Umbrella plant | Bulrush | Monochoria | Tooth cup |
| 170 | 125 | 0 | 5 | 5 | 3 | 5 | 5 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 172 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 174 | 125 | 0 | 5 | 5 | 4 | 5 | 4 |
|  | 250 | 0 | 5 | 5 | 4 | 5 | 5 |
|  | 500 | 0 | 5 | 5 | 4 | 5 | 5 |
|  | 1000 | 0 | 5 | 5 | 4 | 5 | 5 |
| 175 | 125 | 0 | 5 | 5 | 3 | 5 | 5 |
|  | 250 | 0 | 5 | 5 | 3 | 5 | 5 |
|  | 500 | 0 | 5 | 5 | 4 | 5 | 5 |
|  | 1000 | 0 | 5 | 5 | 4 | 5 | 5 |
| 178 | 125 | 0 | 5 | 5 | 4 | 5 | 5 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 181 | 125 | 0 | 5 | 5 | 4 | 5 | 4 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 188 | 125 | 0 | 5 | 5 | 4 | 4 | 3 |
|  | 250 | 0 | 5 | 5 | 4 | 5 | 4 |
|  | 500 | 0 | 5 | 5 | 5 | 5 | 4 |
|  | 1000 | 0 | 5 | 5 | 5 | 5 | 5 |
| 192 | 125 | 0 | 5 | 5 | 1 | 5 | 2 |
|  | 250 | 0 | 5 | 5 | 1 | 5 | 3 |
|  | 500 | 0 | 5 | 5 | 2 | 5 | 3 |
|  | 1000 | 0 | 5 | 5 | 3 | 5 | 4 |
| 195 | 125 | 0 | 5 | 5 | 4 | 5 | 3 |
|  | 250 | 0 | 5 | 5 | 4 | 5 | 4 |
|  | 500 | 0 | 5 | 5 | 5 | 5 | 5 |
|  | 1000 | 0 | 5 | 5 | 5 | 5 | 5 |
| 196 | 125 | 0 | 5 | 5 | 3 | 5 | 4 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 201 | 125 | 0 | 2 | 5 | 3 | 2 | 2 |
|  | 250 | 0 | 4 | 5 | 4 | 4 | 2 |
|  | 500 | 0 | 5 | 5 | 5 | 5 | 3 |
|  | 1000 | 0 | 5 | 5 | 5 | 5 | 5 |
| 203 | 125 | 0 | 4 | 5 | 3 | 4 | 2 |
|  | 250 | 0 | 5 | 5 | 4 | 5 | 3 |
|  | 500 | 0 | 5 | 5 | 4 | 5 | 4 |
|  | 1000 | 0 | 5 | 5 | 5 | 5 | 5 |
| Benthiocarb (Reference agent) | 125 | 1 | 5 | 5 | 2 | 2 | 3 |
|  | 250 | 2 | 5 | 5 | 2 | 2 | 3 |
|  | 500 | 2 | 5 | 5 | 3 | 3 | 4 |
|  | 1000 | 3 | 5 | 5 | 5 | 4 | 5 |
| Not treated | 0 | 0 | 0 | 0 | 0 | 0 | 0 |

EXAMPLE 9

Test for the herbicidal effects under submerged conditions (2)

Paddy field soil was charged in porcelain pots having a diameter of 9 cm, and then water was added. After the soil was tilled, seeds of barnyard grass were sown on the surface of the soil and two bunches of rice plants (variety: Nihonbare) being in 2-leaf stage were transplanted in 1 cm depth. The pots were flooded to give water depth of 2 cm on the next day and predetermined amount of water dispersible powder of the compounds of the present invention, which was dispersed in 10 ml of water, was added dropwise into every pots on the surface of water for the treatment before the germination of and at the time of both 1.2- and 2-leaf stages of barnyard grass. The pots were settled in a greenhouse and received water in proper time intervals. The examination was carried out after 3 weeks from the treatment with the chemicals and the results were evaluated in the similar manner as in Example 8. The results are shown in Table 3.

TABLE 3

| The compounds of the present invention | | Phytotoxicity against rice plant | Herbicidal effects against barnyard grass | | |
|---|---|---|---|---|---|
| No. | Dose (g/10 ares) | | Pre-emergence | 1.2-Leaf stage | 2-Leaf stage |
| 13 | 12.5 | 0 | 5 | — | 5 |
|  | 25 | 0 | 5 | — | 5 |

TABLE 3-continued

| The compounds of the present invention | | Phytotoxicity against rice plant | Herbicidal effects against barnyard grass | | |
|---|---|---|---|---|---|
| No. | Dose (g/10 ares) | | Pre-emergence | 1.2-Leaf stage | 2-Leaf stage |
| | 50 | 0 | 5 | — | 5 |
| | 100 | 0 | 5 | — | 5 |
| 14 | 12.5 | 0 | 5 | — | 5 |
| | 25 | 0 | 5 | — | 5 |
| | 50 | 0 | 5 | — | 5 |
| | 100 | 0 | 5 | — | 5 |
| 15 | 12.5 | 0 | 5 | — | 5 |
| | 25 | 0 | 5 | — | 5 |
| | 50 | 0 | 5 | — | 5 |
| | 100 | 0 | 5 | — | 5 |
| 18 | 12.5 | 0 | 5 | — | 5 |
| | 25 | 0 | 5 | — | 5 |
| | 50 | 0 | 5 | — | 5 |
| | 100 | 0 | 5 | — | 5 |
| 20 | 12.5 | 0 | 2 | 2 | — |
| | 25 | 0 | 3 | 3 | — |
| | 50 | 0 | 4 | 3 | — |
| | 100 | 0 | 5 | 4 | — |
| 23 | 12.5 | 0 | 5 | 4 | — |
| | 25 | 0 | 5 | 4 | — |
| | 50 | 0 | 5 | 5 | — |
| | 100 | 0 | 5 | 5 | — |
| 28 | 12.5 | 0 | 5 | 5 | — |
| | 25 | 0 | 5 | 5 | — |
| | 50 | 0 | 5 | 5 | — |
| | 100 | 0 | 5 | 5 | — |
| 34 | 12.5 | 0 | 5 | 4 | — |
| | 25 | 0 | 5 | 5 | — |
| | 50 | 0 | 5 | 5 | — |
| | 100 | 0 | 5 | 5 | — |
| 37 | 12.5 | 0 | 4 | 4 | — |
| | 25 | 0 | 5 | 5 | — |
| | 50 | 0 | 5 | 5 | — |
| | 100 | 0 | 5 | 5 | — |
| 49 | 12.5 | 0 | 2 | 1 | — |
| | 25 | 0 | 4 | 3 | — |
| | 50 | 0 | 5 | 4 | — |
| | 100 | 0 | 5 | 4 | — |
| 50 | 12.5 | 0 | 5 | 4 | — |
| | 25 | 0 | 5 | 5 | — |
| | 50 | 0 | 5 | 5 | — |
| | 100 | 0 | 5 | 5 | — |
| 51 | 12.5 | 0 | 5 | 5 | — |
| | 25 | 0 | 5 | 5 | — |
| | 50 | 0 | 5 | 5 | — |
| | 100 | 0 | 5 | 5 | — |
| 53 | 12.5 | 0 | 4 | 4 | — |
| | 25 | 0 | 5 | 5 | — |
| | 50 | 0 | 5 | 5 | — |
| | 100 | 0 | 5 | 5 | — |
| 54 | 12.5 | 0 | 4 | 4 | — |
| | 25 | 0 | 5 | 5 | — |
| | 50 | 0 | 5 | 5 | — |
| | 100 | 0 | 5 | 5 | — |
| 58 | 12.5 | 0 | 5 | 5 | — |
| | 25 | 0 | 5 | 5 | — |
| | 50 | 0 | 5 | 5 | — |
| | 100 | 0 | 5 | 5 | — |
| 78 | 12.5 | 0 | 4 | 2 | — |
| | 25 | 0 | 5 | 4 | — |
| | 50 | 0 | 5 | 5 | — |
| | 100 | 0 | 5 | 5 | — |
| 87 | 12.5 | 0 | 5 | 5 | — |
| | 25 | 0 | 5 | 5 | — |
| | 50 | 0 | 5 | 5 | — |
| | 100 | 0 | 5 | 5 | — |
| 92 | 12.5 | 0 | 5 | 5 | — |
| | 25 | 0 | 5 | 5 | — |
| | 50 | 0 | 5 | 5 | — |
| | 100 | 0 | 5 | 5 | — |
| 96 | 12.5 | 0 | 5 | 3 | — |
| | 25 | 0 | 5 | 3 | — |
| | 50 | 0 | 5 | 4 | — |
| | 100 | 0 | 5 | 5 | — |
| 101 | 12.5 | 0 | 5 | 5 | — |
| | 25 | 0 | 5 | 5 | — |
| | 50 | 0 | 5 | 5 | — |
| | 100 | 0 | 5 | 5 | — |

TABLE 3-continued

| The compounds of the present invention | | Phytotoxicity against rice plant | Herbicidal effects against barnyard grass | | |
|---|---|---|---|---|---|
| No. | Dose (g/10 ares) | | Pre-emergence | 1.2- Leaf stage | 2- Leaf stage |
| 102 | 12.5 | 0 | 5 | 5 | — |
|  | 25 | 0 | 5 | 5 | — |
|  | 50 | 0 | 5 | 5 | — |
|  | 100 | 0 | 5 | 5 | — |
| 113 | 12.5 | 0 | 5 | 5 | — |
|  | 25 | 0 | 5 | 5 | — |
|  | 50 | 0 | 5 | 5 | — |
|  | 100 | 0 | 5 | 5 | — |
| 125 | 12.5 | 0 | 5 | 2 | — |
|  | 25 | 0 | 5 | 2 | — |
|  | 50 | 0 | 5 | 4 | — |
|  | 100 | 0 | 5 | 5 | — |
| Benthiocarb (Reference agent) | 12.5 | 0 | 2 | 1 | 1 |
|  | 25 | 0 | 3 | 2 | 2 |
|  | 50 | 0 | 4 | 2.5 | 2.5 |
|  | 100 | 1 | 5 | 4 | 4 |
| Not treated |  | 0 | 0 | 0 | 0 |

EXAMPLE 10

Test for the Herbicidal Effects by the Surface Treatment of Farmland Soil

Farmland soil was charged into porcelain pots having a diameter of 12 cm and several kinds of crop seeds together with weed seeds were sown. The seeds were further covered by the soil in 1 cm thickness. Predetermined amount of water dispersible powder of the compounds of the present invention, which was dispersed in 10 ml of water per every pots, was sprayed on the surface of soil for the treatment. The pots were stationarily placed in a greenhouse and received sprayed water in proper time intervals. After 3 weeks from the treatment with the chemicals, the herbicidal effects and the influences against soybean and cotton plants were examined in the similar manner as in Example 8. The results are shown in Table 4.

TABLE 4

| The compounds of the present invention | | Phytotoxicity | | Herbicidal effects | | |
|---|---|---|---|---|---|---|
| No. | Dose (g/10 ares) | Soybean plant | Cotton plant | Barnyard grass | Crab grass | Foxtail |
| 13 | 50 | 0 | 0 | 4.5 | 5 | 4.5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 14 | 50 | 0 | 0 | 4.5 | 5 | 4.5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 15 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 18 | 50 | 0 | 0 | 4 | 5 | 4 |
|  | 100 | 0 | 0 | 5 | 5 | 5 |
|  | 200 | 0 | 0 | 5 | 5 | 5 |
|  | 400 | 0 | 0 | 5 | 5 | 5 |
| 20 | 50 | 0 | 0 | 2 | 3 | 2 |
|  | 100 | 0 | 0 | 3 | 4 | 4 |
|  | 200 | 0 | 0 | 4 | 5 | 4 |
|  | 400 | 0 | 0 | 4 | 5 | 4 |
| 23 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 28 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 34 | 50 | 0 | 0 | 4 | 5 | 4 |
|  | 100 | 0 | 0 | 4 | 5 | 5 |
|  | 200 | 0 | 0 | 5 | 5 | 5 |
|  | 400 | 0 | 0 | 5 | 5 | 5 |
| 37 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 49 | 50 | 0 | 0 | 2 | 3 | 2 |
|  | 100 | 0 | 0 | 3 | 5 | 3 |
|  | 200 | 0 | 0 | 4 | 5 | 3 |
|  | 400 | 0 | 0 | 4 | 5 | 4 |

TABLE 4-continued

| The compounds of the present invention | | Phytotoxicity | | Herbicidal effects | | |
|---|---|---|---|---|---|---|
| No. | Dose (g/10 ares) | Soybean plant | Cotton plant | Barnyard grass | Crab grass | Foxtail |
| 50 | 50 | 0 | 0 | 4 | 5 | 4 |
|  | 100 | 0 | 0 | 4.5 | 5 | 5 |
|  | 200 | 0 | 0 | 5 | 5 | 5 |
|  | 400 | 0 | 0 | 5 | 5 | 5 |
| 51 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 53 | 50 | 0 | 0 | 4 | 5 | 4 |
|  | 100 | 0 | 0 | 5 | 5 | 5 |
|  | 200 | 0 | 0 | 5 | 5 | 5 |
|  | 400 | 0 | 0 | 5 | 5 | 5 |
| 54 | 50 | 0 | 0 | 4 | 5 | 4 |
|  | 100 | 0 | 0 | 5 | 5 | 5 |
|  | 200 | 0 | 0 | 5 | 5 | 5 |
|  | 400 | 0 | 0 | 5 | 5 | 5 |
| 58 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 78 | 50 | 0 | 0 | 3 | 4 | 3 |
|  | 100 | 0 | 0 | 4 | 5 | 4 |
|  | 200 | 0 | 0 | 5 | 5 | 4 |
|  | 400 | 0 | 0 | 5 | 5 | 5 |
| 87 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 92 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 96 | 50 | 0 | 0 | 4 | 5 | 4 |
|  | 100 | 0 | 0 | 5 | 5 | 5 |
|  | 200 | 0 | 0 | 5 | 5 | 5 |
|  | 400 | 0 | 0 | 5 | 5 | 5 |
| 101 | 50 | 0 | 0 | 5 | 5 | 5 |
|  | 100 | 0 | 0 | 5 | 5 | 5 |
|  | 200 | 0 | 0 | 5 | 5 | 5 |
|  | 400 | 0 | 0 | 5 | 5 | 5 |
| 102 | 50 | 0 | 0 | 4 | 5 | 4 |
|  | 100 | 0 | 0 | 5 | 5 | 5 |
|  | 200 | 0 | 0 | 5 | 5 | 5 |
|  | 400 | 0 | 0 | 5 | 5 | 5 |
| 113 | 50 | 0 | 0 | 4 | 5 | 4 |
|  | 100 | 0 | 0 | 5 | 5 | 5 |
|  | 200 | 0 | 0 | 5 | 5 | 5 |
|  | 400 | 0 | 0 | 5 | 5 | 5 |
| 125 | 50 | 0 | 0 | 4 | 4 | 4 |
|  | 100 | 0 | 0 | 4 | 5 | 4 |
|  | 200 | 0 | 0 | 5 | 5 | 5 |
|  | 400 | 0 | 0 | 5 | 5 | 5 |
| Benthiocarb (Reference agent) | 50 | 0 | 0 | 3 | 4 | 3 |
|  | 100 | 0 | 0 | 4 | 5 | 4 |
|  | 200 | 0 | 0 | 5 | 5 | 5 |
|  | 400 | 0 | 0 | 5 | 5 | 5 |
| Not treated |  | 0 | 0 | 0 | 0 | 0 |

What is claimed is:

1. A carbamate compound of the formula (I)

wherein

X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or phenyl having one or more substituents which may be the same or different, and are selected from the group consisting of halogen, lower alkyl, lower alkenyl, lower alkoxy, lower alkenyloxy, lower alkynyloxy, lower alkylthio, lower alkylamino, (hydroxy)-lower alkyl, (lower alkoxy)-lower alkyl, ($C_1$–$C_2$) acyl, nitro, cyano, methylenedioxy, and halogenated lower alkyl, Y is an oxygen atom or a sulfur atom, Z is lower alkyl, W is pyridyl substituted by one or two of the same substituents selected from the group consisting of halogen, lower alkyl, and lower alkylamino when X is 2-naphthyl but W is pyridyl which may be substituted by one or two of the same or different substituents selected from the group consisting of halogen, nitro, lower alkyl, lower alkoxy, lower alkylthio, and lower alkylamino when X is other than 2-naphthyl.

2. The carbamate of claim 1, wherein

X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or phenyl having one to three of the same or different substituents selected from the group consisting of halogen, lower alkyl, lower alkenyl, lower alkoxy, lower alkenyloxy, lower alkynyloxy, lower alkylthio, lower alkylamino, (hydroxy)-lower alkyl, (lower alkoxy)-lower alkyl, (C$_1$–C$_2$) acyl, nitro, cyano, methylenedioxy, and halogenated lower alkyl.

3. The carbamate of claim 2, wherein

X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or phenyl having one to three of the same or different substituents selected from the group consisting of a chlorine atom, a bromine atom, alkyl of 1 to 6 carbon atoms, alkenyl of 3 carbon atoms, alkoxy of 1 to 4 carbon atoms, alkenyloxy of 3 carbon atoms, alkynyloxy of 3 carbon atoms, methylthio, dimethylamino, hydroxymethyl, hydroxyethyl, methoxymethyl, acyl of 1 to 2 carbon atoms, nitro, cyano, methylenedioxy, trifluoromethyl, and bromoethyl.

4. The carbamate of claim 1, wherein
Z is alkyl of 1 to 3 carbon atoms.

5. The carbamate of claim 1, wherein
W is pyridyl substituted by one or two of the same substituents selected from the group consisting of a chlorine atom, alkyl of 1 to 2 carbon atoms, and dimethylamino when X is 2-naphthyl but W is pyridyl which may be substituted by one or two of the same or different substituents selected from the group consisting of
a chlorine atom, a bromine atom, nitro, alkyl of 1 to 2 carbon atoms, methoxy, ethoxy, methylthio, methylamino, and dimethylamino when X is other than 2-naphthyl.

6. The carbamate of claim 1, wherein

X is 2-naphthyl, 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or phenyl having one to three of the same or different substituents selected from the group consisting of a chlorine atom, a bromine atom, alkyl of 1 to 6 carbon atoms, alkenyl of 3 carbon atoms, alkoxy of 1 to 4 carbon atoms, alkenyloxy of 3 carbon atoms, alkynyloxy of 3 carbon atoms, methylthio, dimethylamino, hydroxy-methyl, hydroxyethyl, methoxymethyl, acyl of 1 to 2 carbon atoms, nitro, cyano, methylenedioxy, trifluoromethyl, and bromoethyl, Y is an oxygen atom or a sulfur atom, Z is alkyl of 1 to 3 carbon atoms, W is pyridyl substitued by one or two of the same substituents selected from the group consisting of a chlorine atom, alkyl of 1 to 2 carbon atoms, and dimethylamino when X is 2-naphthyl but W is pyridyl which may be substituted by one or two of the same or different substituents selected from the group consisting of a chlorine atom, a bromine atom, nitro, alkyl of 1 to 2 carbon atoms, methoxy, ethoxy, methylthio, methylamino, and dimethylamino when X is other than 2-naphthyl.

7. A herbicide comprising
the carbamate of formula (I)

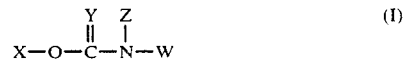

as an active ingredient, and
a carrier.

8. A herbicide of claim 7 further comprising 3',4'-dichloropropionanilide.

9. The herbicide of claim 8 wherein the carbamate is O-3-tert-butylphenyl N-(6-methoxy-2-pyridyl)-N-methylthiocarbamate.

* * * * *